US012742207B2

(12) United States Patent
Wang

(10) Patent No.: US 12,742,207 B2
(45) Date of Patent: Sep. 22, 2026

(54) FLUORESCENT CROSS-LINKED RNase H MUTANT CONJUGATE, miRNA COMBINATION AND APPLICATION THEREOF

(71) Applicant: SHANGHAI MIRAN BIOTECH CO., LTD., Shanghai (CN)

(72) Inventor: Yiran Wang, Shanghai (CN)

(73) Assignee: SHANGHAI MIRAN BIOTECH CO., LTD., Shanghai (CN)

( * ) Notice: Subject to any disclaimer, the term of this patent is extended or adjusted under 35 U.S.C. 154(b) by 790 days.

(21) Appl. No.: 18/003,672

(22) PCT Filed: Jul. 12, 2021

(86) PCT No.: PCT/CN2021/105838

§ 371 (c)(1),
(2) Date: Dec. 28, 2022

(87) PCT Pub. No.: WO2022/007970

PCT Pub. Date: Jan. 13, 2022

(65) Prior Publication Data

US 2023/0242994 A1 Aug. 3, 2023

(30) Foreign Application Priority Data

Jul. 10, 2020 (CN) ......................... 202010663579.5
Sep. 30, 2020 (CN) ......................... 202011058041.8
Dec. 1, 2020 (CN) ......................... 202011389005.X
Dec. 1, 2020 (CN) ......................... 202011400346.2

(51) Int. Cl.

*C12N 9/22* (2006.01)
*C07K 19/00* (2006.01)
*C12Q 1/6837* (2018.01)
*C12Q 1/6886* (2018.01)

(52) U.S. Cl.

CPC ............ *C12Q 1/6886* (2013.01); *C07K 19/00* (2013.01); *C12N 9/22* (2013.01); *C12Y 301/26004* (2013.01); *C12Q 1/6837* (2013.01); *C12Q 2600/158* (2013.01); *C12Q 2600/178* (2013.01)

(58) Field of Classification Search

None
See application file for complete search history.

(56) References Cited

U.S. PATENT DOCUMENTS 7,560,232 B2 7/2009 Carter et al.
11,584,960 B2 2/2023 Litterst et al.
2004/0248145 A1 12/2004 Crooke et al.
2011/0143953 A1 6/2011 Johnston et al.
2014/0322789 A1 10/2014 Lee
2018/0092993 A1 4/2018 Desai et al.
2018/0169255 A1 6/2018 Gao et al.
2020/0147156 A1 5/2020 Greenberg et al.
2023/0242994 A1 8/2023 Wang

FOREIGN PATENT DOCUMENTS

| | | | |
|---|---|---|---|
| CA | 3069821 | A1 | 1/2019 |
| CA | 3070299 | A1 | 1/2019 |
| CN | 101768625 | A | 7/2010 |
| CN | 103305602 | A | 9/2013 |
| CN | 106459205 | A | 2/2017 |
| CN | 109844538 | A | 6/2019 |
| CN | 111051531 | A | 4/2020 |
| CN | 112501295 | A | 3/2021 |
| JP | 2006-510371 | A | 3/2006 |
| JP | 2010-507099 | A | 3/2010 |
| JP | 2023532378 | A | 7/2023 |

OTHER PUBLICATIONS

Singh et al. (Curr. Protein Pept. Sci. 18:1-11, 2017).*
Zhang et al. (Structure 26:1474-1485, 2018).*
Jan. 30, 2024 Notice of Reasons for Refusal issued in Japanese Patent Application No. 2023-501366.
Tatiana et al., "R Loops: From Physiological to Pathological Roles," Cell 179, pp. 604-618, 2019.
Jia-Yu Chen et al., R-ChIP for genome-wide mapping of R-loops by using catalytically inactive RNASEH1, Nat Protoc. 14(5)1661-1685, 2019.
Vaibhav Bhatia et al., "BRCA2 prevents R-loop accumulation and associates with TREX-2 mRNA export factor PCID2," nature, vol. 511, p. 362-365, 2014.
Extended European Search Report issued by EPO for a corrsponding European patent application No. 21838258.8 dated Nov. 25, 2024.
First Office Action issued by CNIPA for a corresponding Chinese patent application No. 202011389005X dated Dec. 18, 2024.
First Search Report issued by CNIPA for a corresponding Chinese patent application No. 202011389005X ated Dec. 18, 2024.

(Continued)

*Primary Examiner* — Richard G Hutson
(74) *Attorney, Agent, or Firm* — MH2 Technology Law Group LLP

(57) ABSTRACT

A fluorescent cross-linked RNase H mutant conjugate, a miRNA combination and an application thereof. The fluorescent cross-linked RNase H mutant conjugate (i) is as represented by RNase Hv-(Lx-SH-F)n or (ii) comprises an RNase Hv-Lx-ligand and receptor-F, wherein the ligand can bind to the receptor, RNase Hv is an RNase H mutant, which can bind to RNA or RNA-DNA hybrid strands, but cannot cleave RNA; L is a linker, and x is 1-10; SH is an amino acid containing a sulfhydryl group; F is a luminescent functional group, and n is 1-7. The fluorescent cross-linked RNase H mutant conjugate can directly recognize DNA/RNA hybrid strands and can be converted to generate detectable signals without PCR amplification, and can be applied to sensitively and quickly detect RNA.

14 Claims, 9 Drawing Sheets

Specification includes a Sequence Listing.

(56) References Cited

OTHER PUBLICATIONS

Marc Torrent et al. "Comparison of the membrane interaction mechanism of two antimicrobial RNases: RNase 3/ECP and RNase 7" Biochimica etBiophysica Acta (BBA)—Biomembranes, vol. 1788 (2009) 1116-1125.
Katsuo Katayanagi et al. Crystal Structures of Ribonuclease HI Active Site Mutants from *Escherichia coli* The Journal of Biological Chemistry, vol. 268, No. 29, Issue of Oct. 15, pp. 22092-22099, 1993.
May 24, 2024 The partial supplementary European search report issued in European Patent Application No. 21838258.8.
Kanaya S et al:"Function and Structures of Rebonuclease H Enzymes", Subcellular Biochemistry, XX, XX, vol. 24, Jan. 1, 1995 (Jan. 1, 1995), pp. 377-422.
Sep. 28, 2021 International Search Report issued in International Patent Application No. PCT/CN2021/105838.
Sep. 28, 2021 Written Opinion of the International Searching Authority issued in International Patent Application No. PCT/CN2021/105838.
Cui et al., Acta Pharmacologica Sinica, vol. 34, 2013, pp. 309-313.
Deng et al., Chem. Sci., vol. 8, No. 5, 2017, pp. 3668-3675 Highly specific imaging of mRNA in single cells by target RNA-initiated rolling circle amplification.
Yao et al., Curr Opin Chem Biol., vol. 51, 2019, pp. 11-17 The roles of microRNAs in epigenetic regulation.
Zhang et al., Chem. Sci., vol. 11, 2020, pp. 3812-3819 Simultaneous and ultrasensitive detection of multiple microRNAs by single-molecule fluorescence imaging.
Liu et al., Annual of Oncology, vol. 31, 2020, pp. 745-759 Sensitive and specific multi-cancer detection and localization using methylation signatures in cell-free DNA.
Tentori et al., Lab Chip, vol. 18, No. 16, 2018, pp. 2410-2424 Quantitative and multiplex microRNA assays from unprocessed cells in isolated nanoliter well arrays.
Liu et al., Biomed Res.Int., 2017, pp. 2013989 The Combination of the Tumor Markers Suggests the Histological Diagnosis of Lung Cancer.
Gilad et al., J Mol Diagn, vol. 14, 2012, pp. 510-517 Classification of the Four Main Types of Lung Cancer Using a MicroRNA-Based Diagnostic Assay.
Jayaprakash et al., Nucleic Acids Res., vol. 39, No. 21, 2011, pp. e141 Identification and remediation of biases in the activity of RNA ligases in small-RNA deep sequencing.
Pohlmann et al., Anal Chem, vol. 82, 2010, pp. 4434-4440 Electrochemical Detection of MicroRNAs via Gap Hybridization Assay.
Raabe et al., Nucleic Acids Res., vol. 42, No. 3, 2014, pp. 1414-1426 Biases in small RNA deep sequencing data.
Gallardo et al., Carcinogenesis, vol. 30, 2009, pp. 1903-1909 miR-34a as a prognostic marker of relapse in surgically resected non-small-cell lung cancer.
Hayes et al., Trends in Molecular Medicine, vol. 20, 2014, pp. 460-469 MicroRNAs in cancer biomarkers, functions and therapy.
Fehlmann et al., JAMA Oncol., vol. 6, No. 5, 2020, pp. 714-723 Evaluating the Use of Circulating MicroRNA for Lung Cancer Detection in Symptomatic Patients.
IQBAL, Mol Aspects Med., vol. 17, 2018, pp. 0098-2997 MicroRNA in lung cancer role, mechanisms, pathways and therapeutic relevance.
Microsyst Nanoeng, vol. 6, 2020, pp. 51 Spatially resolved and multiplexed MicroRNA quantification from issue using nanoliter well arrays.
Hassanein, Cancer Prev Res., vol. 5, No. 8, 2012, pp. 992-1006 The State of Molecular Biomarkers for the Early Detection of Lung Cancer.
Taylor, Ann Oncol., vol. 31, No. 9, 2020, pp. 1266-1267.
Chuang et al., Pediatric Research, vol. 61, 2007, pp. 24-29 Epigenetics and MicroRNAs.
Lebanony et al., J Clin Oncol, vol. 27, 2009, pp. 2030-2037 Diagnostic Assay Based on hsa-miR-205 Expression Distinguishes Squamous From Nonsquamous Non-Small-Cell Lung Carcinoma.
Kibriya et al., Cancer Epidemiol Biomarkers Prev, vol. 23, No. 12, 2014, pp. 2667-2672 Measurement of telomere length a new assay using QuantiGene chemistry on a Luminex platform.
Hu et al., Nucleic Acids Res., vol. 34, No. 7, 2006, pp. e52 An antibody-based microarray assay for small RNA detection.
Levin et al., Nat Methods, vol. 7, No. 9, 2010, pp. 709-715 Comprehensive comparative analysis of strand-specific RNA sequencing methods.
Zhang Pingping et al, Military Medicine, vol. 36, 2012, pp. 173-177 Advances in Research on Multiple Biological Detecting Technology.
Marzi et al. Optimization and Standardization of Circulating MicroRNA Detection for Clinical Application The miR-Optimization and Standardization of Circulating MicroRNA.
Wang et al., Molecular and Cellular Probes, vol. 24, 2010, pp. 15-19—Enhancing allele-specific PCR for specifically detecting short deletion and insertion DNA mutations.
Bracken et al., Nat Rev Genet., vol. 17, 2016, pp. 719-732 A network-biology perspective of microRNA function and dysfunction in cancer.
Garcia-Muse, T. et al. Cell, vol. 17917 Oct. 2019(Oct. 17, 2019),pp. 604-618 R Loops: From Physiological to Pathological Roles.
Chen, J.Y. et al. Nature Protocol, vol. 14No.502 Jul. 2019(Jul. 2, 2019)pp. 1661-1685 R-ChIP for genome-wide mapping ofR-loops by using catalytically inactive RNASEH1.
Bhatiav.et al. Nature, vol. 511,Jul. 17, 2014(Jul. 17, 2014)pp. 362-365 BRCA2 prevents R-loop accumulation and associates with TREX-2 mRNA export factor PCID2.
Bekkaoui,F. et al. Bio Techniques, vol. 20, No. 229 Feb. 1996(Feb. 29, 1996)pp. 240-248 Cycling Probe Technology with RNase H Attached to an Oligonucleotide.
Chinese Priority Application No. 202011389005.X.
Chinese Priority Application No. 202010663579.5.
Chinese Priority Application No. 202011058041.8.
Chinese Priority Application No. 202011400346.2.

* cited by examiner

FLUORESCENT CROSS-LINKED RNase H MUTANT CONJUGATE, miRNA COMBINATION AND APPLICATION THEREOF

REFERENCE TO SEQUENCE LISTING

The Sequence Listing is submitted concurrently with the specification as an ASCII formatted text file via EFS-Web, with a file name of "P22418027US-2-SEQ", a creation date of Dec. 9, 2022, and a size of 10,612 bytes. The Sequence Listing filed via EFS-Web is part of the specification and is incorporated in its entirety by reference herein.

The present application is a National Stage of International Application No. PCT/CN2021/105838, filed on Jul. 12, 2021, which claims the priorities of Chinese patent application No. 202010663579.5 filed on Jul. 10, 2020, Chinese patent application No. 202011058041.8 filed on Sep. 30, 2020, Chinese patent application No. 202011389005.X filed on Dec. 1, 2020, and Chinese patent application No. 202011400346.2 filed on Dec. 1, 2020. The contents of the Chinese patent applications are incorporated herein by reference in their entireties.

TECHNICAL FIELD

The present disclosure belongs to the field of biological detection, relates to a fluorescent cross-linked RNase H mutant conjugate and an application thereof in detecting RNA, in particular to a technology for simultaneous detection of one or more miRNA combinations of a disease; and to a miRNA combination, a kit containing the same and an application thereof in the diagnosis of lung cancer.

BACKGROUND

Early diagnosis of tumors and other chronic diseases has received increasing attention. Novel tumor diagnostic biomarkers include ctDNA and RNA. The latest clinical research progress showed that RNA biomarkers, especially Micro RNA (miRNA), have more obvious advantages in the diagnosis of early-stage tumors, mainly reflected in sensitivity and specificity (Liu et al. Ann. Onc., 2020, 31(6), 745-759; Fehlmann, et al., JAMA Oncol. 2020, 6(5), 714-723). miRNAs are a class of endogenous small RNAs with a length of about 19-25 nucleotides, which undertake key regulatory functions in important processes such as embryonic development, cell differentiation and organogenesis. Therefore, monitoring the role of miRNA biomarkers in tumor occurrence and development is the basis for their use as tumor diagnosis, prognostic markers and therapeutic targets. miRNAs in peripheral blood are ideal targets for non-invasive liquid biopsy, which can realize early diagnosis of patients and facilitate dynamic and serial monitoring. However, the analysis or detection of small RNAs, especially miRNAs, is still a difficult problem.

Existing methods for analyzing or detecting RNA include real-time PCR fluorescence detection based on the principle of PCR amplification or gene chip hybridization detection methods after reverse transcription PCR. These existing methods have systematic bias due to the need for ligation followed by PCR amplification to detect target miRNAs (for details, see Raabe et al., Nucleic Acids Res. 2014, 42(3), 1414-1426; Levin et al. Nat Methods. 2010, 7(9), 709-715; Jayaprakash et al, Nucleic Acids Res. 2011, 39(21), e141), or only a few small RNAs with limited throughput can be recognized, which cannot achieve rapid, accurate, economical and high-throughput detection and is difficult to transform and apply the RNA biomarkers that are of important value. How to accurately quantify and effectively detect miRNAs in tissues and body fluids has become a common problem for the widely commercial use of this biomarker in disease analysis and drug development. The detection of miRNA without PCR amplification is the key to solve this common problem. The method of miRNA detection without PCR amplification uses a S9.6 monoclonal antibody (mAb) to recognize a DNA/RNA hybrid strand, and uses a second polyclonal antibody that recognizes S9.6 mAb to generate a detection signal (Hu et al., Nucleic Acids Res. 2006, 34(7), e52). This detection method requires multiple steps of washing and solution addition, and the hybridization condition is 16 hours at 45° C., which is limited in practical application. Another method for detecting RNA without PCR amplification is a gap hybridization method. By hybridizing four single-stranded nucleic acid molecules including a target RNA, a target RNA sequence that can be detected depends on the sequence of a longest complementary probe. For different RNAs, a detection system needs to use complementary probes with different sequences. Therefore, only a limited number of miRNAs with a limited sequence range can be recognized and this method cannot be used as a general-purpose miRNA detection technology (Pohlmann et al., 2010, Anal Chem, 82, 4434-4440). Another gap hybridization method developed by panomics, a subsidiary of Thermo, is QuantiGene chemistry, which is not only limited by the relevant detection probes, but also needs to carry out an RNA/DNA hybridization reaction at 54° C. for 20 hours, posing a great challenge to the thermal stability of RNA. The detection process requires multiple washings and reagent additions, which has great application limitations (Kibriya et al., Cancer Epidemiol Biomarkers Prev, 2014, 23(12), 2667-2672).

Therefore, there is an urgent need for an RNA detection technology that can directly recognize a DNA/RNA hybrid strand in one step and convert the DNA/RNA hybrid strand to generate a detectable signal. Carter et al. applied a mutated RNase H to detect RNA sequences by recognizing DNA/RNA hybrids (U.S. Pat. No. 7,560,232B2, Methods of capturing, detecting and quantifying RNA DNA hybrids and a modified RNase H useful therein). However, this method cannot meet the needs of practical application scenarios in terms of the sensitivity, convenience and practicability in detecting RNA.

In addition, tumors, other chronic diseases, and public health emergencies require rapid and accurate screening, recognition, analysis, or detection of samples. Multiple biomarker detection is mainly simultaneous detection of multiple biomarker targets that exist or are suspected to exist in a single sample. Using single-target detection technology to analyze multiple targets in a single sample requires to perform multiple repeated operations on the same sample, which will not only increase the workload, prolong the detecting period, increase the risk of sample contamination and the risk of detecting personnel safety and biosafety, but most importantly, will bring great challenges to the reliability of detecting results. Therefore, multiple biological detecting technology for different targets of the same type is extremely critical (Zhang Pingping et al., Advances in Research on Multiple Biological Detecting Technology, Military Medicine, 2012, 36, 173-177).

With the development of instruments capable of high-throughput detection of biomarkers, clinically relevant diagnostic detection has developed from meeting the basic detection requirements of sensitivity and specificity to multi-dimensional requirements of assay performance (sensitivity, specificity, reproducibility, reliability of results and sample demand) and operational performance (simple, fast). Biomarkers for clinical diagnosis have also progressed from the most basic cytokines recognized by antigen-antibody reaction (such as tumor biomarkers CEA, PSA, etc.) to the detection of nucleic acid mutations by PCR, such as SNP, TMB, etc. With the in-depth development of modern biotechnology, the demand for disease understanding and monitoring has progressed from cytokine changes and nucleic acid mutation detection to the latest omics-level research, such as RNA expression profiling/epigenetics, etc. (Chinese Patent 201880058078, Multiplex detection of short nucleic acids; Chuang et al. Pediatric Research, 2007, 61, 24-29; Fransquet et al., 58, 5-14; Yao et al., Curr Opin Chem Biol. 2019, 51, 11-17).

The latest clinical research progress shows that RNA biomarkers, especially Micro RNA (miRNA), have more obvious advantages in the diagnosis of early-stage tumors, mainly reflected in sensitivity and specificity (Liu et al., Annual of Oncology, 2020, 31, 745-759; Fehlmann, et al., JAMA Oncol. 2020, 6, 714-723). The same miRNA can affect multiple protein-coding genes, and the same gene can be affected by multiple miRNAs in a complex network manner. Therefore, monitoring the role of miRNA biomarkers in tumor occurrence and development is the basis for their use as tumor diagnosis, prognostic biomarkers and therapeutic targets. miRNA biomarkers in body fluids are ideal targets for non-invasive liquid biopsy, enabling early diagnosis of patients and facilitating dynamic and serial monitoring (Bracken et al., Nat Rev Genet. 2016, 17, 719-732; Hayes et al., Trends in Molecular Medicine 2014, 20, 460-469; Lebanony et al., J Clin Oncol, 2009, 27, 2030-2037; Gilad et al., J Mol Diagn, 2012, 14, 510-517). In summary, miRNA biomarkers that can meet these needs all require the detection of multiple miRNA targets.

A variety of detection methods for RNA (miRNA) expression levels have been developed. There are many miRNA detection methods based on the principle of PCR. Quantitative real-time PCR is the most commonly used method for miRNA quantitative detection. Other commonly used methods include stem-loop RT-PCR method, polyA tail-based RT-PCR method and so on. However, the detection data of specific miRNA expression levels obtained from quantitative PCR by different researchers varied greatly. Marzi et al. reported that the content of miR-34a in blood was too low to be detected, thus synthetic exogenous miR-34a was added as an external reference (Marzi et al., Clinical Chemistry, 2016, 62, 743-754), by contrast, assays performed by several other research groups showed that miR-34a can be easily detected (Cui et al., Acta Pharmacologica Sinica, 2013, 34, 309-313; Gallardo et al., Carcinogenesis, 2009, 30, 1903-1909). In view of the inconsistence from the assay results of miRNA biomarkers, in addition to the need to address the factors of the RT-PCR system itself, a technology that can simultaneously detect multiple miRNAs in a single tube can avoid diametrically opposite detection results (Tentori et al, Lab Chip, 2018, 18(16), 2410-2424; Microsyst Nanoeng, 2020, 6, 51; Zhang et al, Chem. Sci., 2020, 11, 3812-3819).

Multiplex miRNA detection technology is the focus of the miRNA detection field, but there is currently no mature system for universal, rapid and high-throughput detection. The QuantiGene plex developed by panomics, a subsidiary of Thermo, has achieved the simultaneous determination of 3-80 kinds of mRNA (message RNA) in a single well. However, for the multiplex assay of miRNA, because the length of miRNA is limited to only 19-25 nucleotides, the system cannot achieve the goal of single-well simultaneous multiplex detection: each reaction well can only measure one kind of miRNA (QuantiGene™ Singleplex microRNA, www. .thermofisher.com).

In addition, lung cancer is the malignant tumor with the highest morbidity and mortality, accounting for more than 20% of all cancer mortality. There are more than 800,000 new cases of lung cancer in China each year, and 60-80% of which are in the advanced stage. The 5-year survival rate of early-stage lung cancer patients can reach 90% (stage 0) to 60% (stage I), while that of patients in stages II-IV plummets from 40% to 5%. In the early stage of lung cancer, there are no specific clinical symptoms. 80% of patients with symptoms are in the late stage of disease, missing the optimal treatment period and the surgery opportunity. Therefore, the effective diagnosis of early-stage lung cancer is the key to improve the cure rate and survival rate of lung cancer patients.

The early-stage lung cancers discovered by chest CT appeared as pulmonary nodule. The nature of micronodules and small nodules are difficult to diagnose. Many pulmonary diseases appear as nodules, including tuberculosis, inflammation, infection, mold, segmental atelectasis, bleeding, etc. Distinguishing lung cancer nodule from other benign ones is a huge challenge for lung cancer prevention and treatment. The morbidity of pulmonary nodules is 25-35%, and there are 300 million to 500 million people in China to be investigated. There are many types of nodules, and the current imaging examination is extremely difficult to diagnose in the case of early carcinogenesis, so that patients with early malignant nodules miss the best timing for intervention and treatment. Imaging diagnosis mainly divides the nodules into pure ground-glass nodules, part-solid ground-glass nodules, and pure solid ground-glass nodules according to the density, then combines the analysis of the size, growth rate, internal calcification, vacuole formation, marginal structure of the nodules, peripheral blood vessels and changes in the adjacent pleura, etc., many human artificial influence factors involved. In the 2011 US National Lung Screening Trial (NLST), 39.1% of the low-dose spiral CT screening group were suspected of lung cancer, and it was finally proved that 96.4% of them were false positives and not lung cancer. Therefore, chest imaging can screen for nodules, but not a specific diagnosis of the earliest-stage lung cancer, and repeated inspections cause ionizing radiation exposure damage. Therefore, it is necessary to perform a timely discriminant diagnosis of benign or malignant pulmonary nodules through biomarkers in patients with pulmonary nodules, so that timely clinical intervention can be carried out, which will greatly reduce the incidence of advanced lung cancer and improve the survival rate.

The common early-stage screening and diagnosis of lung cancer mostly rely on tumor biomarkers, chest CT, bronchoscopy, and nodule biopsy. Commonly used lung cancer-related tumor biomarkers include carcinoembryonic antigen (CEA), neuron-specific enolase (NSE), cytokeratin 19 fragment (CYFRA21-1), squamous cell carcinoma antigen (SCC), precursor of gastrin-releasing peptide (Pro-GRP), carbohydrate antigen 125 (CA125), glutathione-S-transferase-π (GST-π), aryl hydrocarbon hydroxylase (AHH), telomerase, etc., but the sensitivity of diagnosis of early-stage lung cancer is very low, leading to missed diagnosis of early-stage lung cancer patients (Liu et al, BioMed Res. Int. 2017, 2013989).

At present, other diagnostic methods, such as CT-guided lesion puncture and various fiberoptic bronchoscopy techniques, are all invasive examinations, which bring certain risks to patients, and have certain requirements on the lesion site and operators. The emerging liquid biopsy technology in recent years can monitor circulating tumor cells (CTCs) and circulating tumor DNA (ctDNA) released into the blood by tumors or metastases, mostly focusing on the research of curative effect and prognosis judgment of lung cancer. Therefore, there is an urgent need to develop non-invasive, accurate and efficient early-stage lung cancer diagnostic markers to help identify malignant lung nodules at an early stage, thereby increasing the early diagnosis rate of lung cancer, reducing lung cancer mortality, reducing medical examination costs, and effectively improving patient's quality of life and serving the public.

Many pioneer biotechnology companies domestically and internationally are developing biomarkers for the diagnosis of pulmonary nodules/early-stage lung cancer, mainly focusing on ctDNA mutation and methylation, autoimmune antibodies and miRNAs, etc. However, nearly all of these novel biomarkers are limited by insufficient sensitivity or difficulty in productization, and cannot meet clinical needs. Taking the current highlighted research and development of biomarker, ctDNA, in the diagnosis of early-stage lung cancer as an example, Grail Bio uses ctDNA methylation as an early-stage lung cancer biomarker, and the diagnostic sensitivity of stage I lung cancer is in the range of 20-40% (Taylor, Ann Oncol. 2020, 31 (9), 1266-1267), which failed to meet the needs of early-stage lung cancer diagnosis, besides its operation difficulty and high detection costs. DNA methylation of genes is used as a lung cancer marker, after sampling from bronchoalveolar lavage fluid, PCR methylation detection is performed on exfoliated cells. The sampling procedure is complicated, the assay itself is cumbersome, and the sensitivity to lung adenocarcinoma is only 66%. The detection of lung cancer performed with seven autoimmune antibodies, represented by Oncoimmune from the UK and CancerProbe from Hangzhou, has a sensitivity of about 40-50%.

miRNAs act biologically in the post-transcriptional stage and are one of the major factors in epigenetics. As a biomarker of early-stage cancer, miRNA has the advantage of sensitivity in the diagnosis of early-stage cancer, and the sensitivity to stage I lung cancer can reach 80-90% (Hassanein, Cancer Prev Res. 2012, 5(8), 992-1006; Iqbal, Mol Aspects Med. 2018, 17, S0098-2997). miRNAs are a class of endogenous small RNAs with a length of about 19-25 nucleotides, which undertake key regulatory functions in important processes such as embryonic development, cell differentiation and organogenesis. Therefore, monitoring the role of miRNA biomarkers in tumor occurrence and development is the basis for their use as tumor diagnosis, prognostic markers and therapeutic targets. miRNAs in peripheral blood are ideal targets for non-invasive liquid biopsy, which can realize early diagnosis of patients and facilitate dynamic continuous monitoring.

However, the analysis or detection of small RNAs, especially miRNAs, is still a challenge. Existing methods for analyzing or detecting RNA include real-time PCR fluorescence assays based on the principle of PCR amplification or gene chip hybridization detection methods after reverse transcription PCR. Due to the systematic bias brought by PCR amplification (Raabe et al., Nucleic Acids Res. 2014, 42(3):1414-1426), these existing methods can only recognize a few small RNAs with limited throughput, and cannot achieve rapid, accurate, economical, and high-throughput detection and is therefore difficult to transform and apply the RNA biomarkers that are of important value. How to accurately quantify and effectively detect miRNAs in tissues and body fluids has become a common problem for the widely commercial use of this biomarker in disease analysis and drug development.

The detection of miRNA without PCR amplification is the key to solve this common problem. Therefore, there is an urgent need for an RNA detection technology that can directly recognize the DNA/RNA hybrid strand in one step and convert the DNA/RNA hybrid strand to generate a detectable signal. Moreover, the method can meet the needs of practical application scenarios in terms of the sensitivity, convenience and practicability of RNA detection (Kibriya et al., Cancer Epidemiol Biomarkers Prev, 2014, 23(12), 2667-2672).

CONTENT OF THE PRESENT INVENTION

In order to solve the defects in the prior arts, lacking RNA detection technology that can directly recognize a DNA/RNA hybrid strand and can convert the DNA/RNA hybrid strand to generate a detectable signal without PCR amplification, the present disclosure provides a fluorescent cross-linked RNase H mutant conjugate and an application thereof; in addition, the present disclosure also provides a miRNA combination, a kit containing the same, and an application thereof in lung cancer diagnosis. In particular, an RNase H mutant modified by specific molecules with similar functions is specifically site-directed cross-linked and modified with a luminescent substance that can produce high signal intensity, providing actual applications that can meet the field of RNA biomarkers' disease research. Herein, a wild-type RNase H may bind to a DNA/RNA hybrid strand (FIG. 1A), and then hydrolyze the bound RNA, and its hydrolysis mechanism is shown in FIG. 1B. The fluorescent cross-linked RNase H mutant conjugate of the present disclosure is obtained by mutation, modification and chemical labeling of RNase H, so as to satisfy the efficient recognition of RNA, especially small RNA, and be used for disease screening, early diagnosis, assessment of therapeutic effect, or analysis and detection relevant to drug development. The detection principle is shown in FIG. 3. A detection probe such as DNA is immobilized on the surface of a carrier, and hybridized with a target RNA in a complementary manner to form a hybrid DNA/RNA strand. This hybrid strand is recognized by fluorescent cross-linked RNase H mutant conjugate. The expression level of the target RNA was obtained by detecting the fluorescence intensity generated on the RNase H mutant conjugate. The present disclosure can detect RNAs with a length of 15-200 nucleotides, including single-stranded RNAs such as a micro RNA (19-25nt), a long non-coding RNA, a message RNA, and a fragment thereof. In addition, the miRNA combination of the present disclosure has high sensitivity and specificity in lung cancer diagnosis. It is well known in the art that if a biomarker or a combination thereof has high sensitivity, then its specificity will be affected; and vice versa. However, one of the highlights of the miRNA combination of the present disclosure is that the miRNA combination can achieve a relative balance between sensitivity and specificity, and has wide applications in preparing a diagnostic reagent for detecting lung cancer or in screening a medicament for treating lung cancer.

In order to solve the above technical problems, the first aspect of the technical solution of the present disclosure is to provide a fluorescent cross-linked RNase H mutant conjugate, wherein, the RNase H mutant conjugate (i) is as represented by RNase Hv-($L_x$-SH-F)$_n$, or (ii) comprises an RNase Hv-Lx-ligand and a receptor-F, the ligand can bind to the receptor; wherein RNase Hv is an RNase H mutant, which can bind to RNA or an RNA-DNA hybrid strand, but cannot cleave RNA; wherein, L is a linker, and x is 1-10; SH is an amino acid containing a sulfhydryl group; F is a luminescent functional group, and n is 1-7.

In a preferred embodiment, in the RNase H mutant conjugate, (i) the SH is cysteine; or (ii) the ligand and the receptor are biotin and streptavidin respectively, or Tag and anti-Tag-Ab respectively;

and/or, the L is a nonpolar amino acid such as alanine, proline, valine, or glycine.

Herein, when the ligand is biotin, an identification mode of biotin is streptavidin-X, and X may be a small molecule, a fluorescent phycoerythrin, a quantum dot, an enzyme, and the like.

In a preferred embodiment, in the RNase H mutant conjugate, $(L_x\text{-SH-F})_n$ or an $L_x$-ligand is linked to C-terminal or N-terminal of the RNase Hv, x is 1-3, n is 3-5; the anti-Tag-Ab is a rabbit antibody or a human antibody, and/or the anti-Tag-Ab is a monoclonal antibody or a polyclonal antibody;

preferably, the Lx is Gly, Gly-Gly, Gly-Gly-Gly, or Ala-Gly; and/or, the Tag is a his Tag.

It is known to those skilled in the art that there is no need to limit the specific sequences or structures of Tag and Ab, as long as the Ab can recognize the Tag and bind to the Tag. Therefore, those skilled in the art should also know that in scheme (ii), the RNase H mutant conjugate is not a conventionally understood conjugate, for example, the Tag and Ab are not connected by a fixed chemical bond, but rely on the non-covalent bonding of the molecular surfaces of Ab and Tag. This non-covalent binding is reversible, that is, a formed complex is not firm and may be dissociated at any time, and the dissociated Tag and Ab still maintain their original physicochemical characteristics and biological activities. For example, the interaction between biotin and avidin is the strongest non-covalent interaction known so far. The affinity constant (K) is $10^{15}$ mol/L, which is at least 10,000 times higher than the affinity between antigen and antibody ($K=10^5$-$10^{11}$ mol/L). Streptavidin may form a streptavidin-phycoerythrin complex with phycoerythrin, thereby recognizing biotin.

In a more preferred embodiment, in the RNase H mutant conjugate, (i) the F is a luminescent substance with an excitation wavelength between 300 nm and 700 nm and an emission wavelength between 300 nm and 700 nm, that can be covalently conjugated to the SH; or, (ii) the F is phycoerythrin and forms a streptavidin-phycoerythrin complex with streptavidin; preferably, (i) the F is a luminescent substance with an excitation wavelength between 480 nm and 580 nm and an emission wavelength between 520 nm and 680 nm. More preferably, the F is Alexa Fluor 555 or Alexa Fluor 532.

In a more preferred embodiment, in the RNase H mutant conjugate, the RNase H is derived from RNase of bacterium, human, or virus. Preferably, the bacteria is *E. coli* K12, and the virus is an HIV virus.

In a more preferred embodiment, in the RNase H mutant conjugate, the RNase Hv undergoes addition, deletion, or replacement of one or more amino acids on a domain of RNase H that catalyzes hydrolysis of RNA, which makes the domain lose function of catalyzing hydrolysis of RNA, but maintain or enhance function of binding to an RNA:DNA hybrid strand. Preferably, the RNase Hv has an amino acid sequence as shown in SEQ ID NO: 20.

In order to solve the above technical problems, the second aspect of the technical solution of the present disclosure is to provide a method for preparing the above RNase H mutant conjugate, wherein when the RNase H mutant conjugate is RNase Hv-$(L_x\text{-SH-F})_n$, then the method comprises following steps:

(1) mixing $(Lx\text{-SH})_n$ and RNase Hv in proportion to conjugate to obtain RNase Hv-$(L_x\text{-SH})_n$;

(2) adding 2-10 times excessive F to the RNase Hv-$(L_x\text{-SH-})_n$ obtained in step (1), thereby producing the RNase Hv-$(L_x\text{-SH-F})_n$; preferably, the F is Alexa Fluor 555 or Alexa Fluor 532.

Preferably, the method further comprises preparing RNase Hv before step (1);

or, the method comprises following steps:

(a) expressing RNase Hv with $(L_x\text{-SH})_n$ at N-terminal or C-terminal to obtain RNase Hv-$(L_x\text{-SH})_n$;

(b) adding 2-10 times excessive F, thereby producing the RNase Hv-$(L_x\text{-SH-F})_n$;

(ii) when the RNase H mutant conjugate comprises an RNase Hv-$L_x$-ligand and a receptor-F, then the method comprises following steps:

(A) expressing the RNase Hv-$L_x$ with $L_x$ at N-terminal or C-terminal; connecting the RNase Hv-$L_x$ with a ligand to form the RNase Hv-$L_x$-ligand;

(B) mixing the receptor with 2-10 times excessive F to produce the receptor-F;

the RNase Hv is preferably an RNase H mutant as shown in SEQ ID NO: 20.

In order to solve the above technical problems, the third aspect of the technical solution of the present disclosure is to provide a kit for RNA detection, wherein the kit comprises the RNase H mutant conjugate.

Preferably, the kit further comprises a DNA probe.

More preferably, the DNA probe is an immobilized DNA probe, and the immobilized DNA probe is immobilized on a microsphere or a flat medium; and/or, the DNA probe has a nucleotide sequence as shown in SEQ ID NO: 1-13.

Further more preferably, 3' end of the immobilized DNA probe is immobilized on the microsphere or the flat medium.

In order to solve the above technical problems, the fourth aspect of the technical solution of the present disclosure is to provide a method for RNA detection comprising following steps:

when an RNase H mutant conjugate is RNase Hv-$(L_x\text{-SH-F})_n$, (1) hybridizing a DNA probe with RNA, and then adding the above RNase H mutant conjugate; or, (2) simultaneously adding a DNA probe and RNA, and the RNase H mutant conjugate as described in the first aspect of the present disclosure, and obtaining a detection result by detecting fluorescence;

when an RNase H mutant conjugate comprises an RNase Hv-Lx-ligand and a receptor-F, simultaneously adding a DNA probe and RNA, and the RNase Hv-$L_x$-ligand as described in the first aspect of the present disclosure, after a hybrid strand formed by DNA and RNA is combined with the RNase Hv-$L_x$-ligand, adding 2-10 times excessive receptor-F, obtaining a detection result by detecting fluorescence.

Preferably, the DNA probe and the RNase H mutant conjugate have a ratio of 2000-100000:1.

More preferably, the RNA detection is a single-tube detection or multi-tube detection of multiplex RNAs; the single-tube detection is to detect one or more kinds of RNAs in one reaction, and the multi-tube detection is to detect only one kind of RNA in each reaction.

Further more preferably, the DNA probe is an immobilized DNA probe, and the immobilized DNA probe is immobilized on a microsphere or a flat medium; and/or, the RNA is mRNA, non-coding RNA or miRNA; more preferably, 3' end of the immobilized DNA probe is immobilized on a microsphere or a flat medium; and/or, the miRNA is a mature miRNA or a precursor miRNA.

The present disclosure provides a universal single-tube quantitative or qualitative analysis or detection method for RNA, especially quantitative or qualitative analysis or detection of multiple miRNAs, so as to achieve sensitive, specific, convenient, accurate, and high-throughput miRNA detection, which meets the needs of multi-dimensional analysis or detection in disease diagnosis, treatment, and new drug development. This system takes a DNA/RNA recognition molecule RH3CF and a sequence-specific DNA probe cross-linked with the surface of microspheres encoded by different fluorescence as a core and simultaneously recognize and analyze a variety of target miRNAs.

The detection of different target RNAs by hybridization methods, especially the detection of miRNA, requires sequence-specific probes. In the detection of multiplex RNA in a single-tube reaction, the probes complementary to the target need to be immobilized on different recognizable media surfaces or specific media locations. The present disclosure adopts carboxylated polystyrene microspheres encoded by different fluorescence chromatography, and after cross-linking probes with different sequences, the specific response target miRNA can be reflected through the encoding or position of a solid phase microspheres. The DNA probe is cross-linked to the surface of a solid-phase carrier, the various encoded microspheres used in a liquid-phase chip can be excited to generate various wavelengths, and their surfaces have been activated to carry carboxyl groups. Therefore, DNA probes with amino-modified ends are prepared, and the probes and microspheres can be cross-linked in a one-step reaction through a chemical cross-linking agent N-(3-dimethylaminopropyl)-N'-ethylcarbodiimide (EDC). The microspheres cross-linked with different DNA probe sequences can be mixed to form the possibility of detecting different miRNAs in a single tube.

The principle of single-tube multiplex RNA simultaneous detection is shown in FIG. 9. The microspheres for different target RNA sequences and encoded by different fluorescence chromatography are first mixed, and a target RNA to be detected and a fluorescent molecular conjugate RH3CF recognized by DNA/RNA are then added. The microsphere probe in the suspension specifically binds to the detected target RNA to form a double strand through DNA/RNA sequence complementary hybridization, and RH3CF binds to the DNA/RNA double strand, so that the DNA/RNA hybrid can be labeled to report fluorescence. The detection and analysis are carried out with a Luminex instrument based on the principle of flow fluorescence detection: the microspheres pass through a microchannel in a single row and are excited by two beams of two-color lasers at the same time: a red laser beam determines the fluorescence code of the microspheres, and the microspheres are classified to identify each different reaction type (i.e. qualitative); another green laser beam measures the fluorescence intensity of the reporter molecules on the microspheres, and determines the number of reporter fluorescent molecules bound on the microspheres, and thus determining the number of target molecules bound on the microspheres (i.e. quantitative). Therefore, the real-time, qualitative and quantitative analysis of the reaction is completed through the simultaneous detection of the two-color laser, thereby realizing the detection of multiplex RNA biomarkers in a single tube of the technology of the present disclosure.

In order to solve the above technical problems, the fifth aspect of the technical solution of the present disclosure is to provide a use of the above RNase H mutant conjugate or the kit in preparation of a reagent for RNA analysis and detection.

Preferably, the RNA is mRNA, non-coding RNA, or miRNA, and/or, the reagent is a diagnostic reagent for cancer detection.

More preferably, the miRNA is a mature miRNA or a precursor miRNA.

In order to solve the above technical problems, the sixth aspect of the technical solution of the present disclosure is to provide a miRNA combination comprising miR-191 and/or miR-454. Preferably, the miRNA combination further comprises miR-1285 and/or miR-126.

In some preferred embodiments, the miRNA combination further comprises miR-181a-2* and/or miR-203a. Preferably, the miRNA combination further comprises miR-15b and/or miR-21. More preferably, the miRNA combination further comprises miR-365 and/or miR-486-5p. Further more preferably, the miRNA combination further comprises miR-375 and/or miR-429.

In some preferred embodiments, the miRNA combination further comprises miR-141 and/or miR-193b. Preferably, the miRNA combination further comprises miR-125b and/or miR-206. More preferably, the miRNA combination further comprises miR-155 and/or miR-574-5p. Further more preferably, the miRNA combination further comprises miR-19a and/or miR-200b.

In order to solve the above technical problems, the seventh aspect of the technical solution of the present disclosure is to provide a composition comprising the miRNA combination of the sixth aspect of technical solution of the present disclosure.

In order to solve the above technical problems, the eighth aspect of the technical solution of the present disclosure is to provide a kit comprising probes for detecting the miRNA combination of the sixth aspect of technical solution of the present disclosure.

In some preferred embodiments, the probes have nucleotide sequences as shown in SEQ ID NO: 1-20. Preferably, 5' end of the probe is a free end, and/or 3' end of the probe is an immobilized end, and preferably, the 3' end is modified with $NH_2$—$C_6$. More preferably, the kit further comprises the miRNA combination of any one of the technical solutions of the present disclosure, and/or the kit further comprises a reagent for detecting CEA, NSE, CYF21-1, SCC, CA125 and/or CA199.

In order to solve the above technical problems, the ninth aspect of the technical solution of the present disclosure is to provide a lung cancer diagnosis system comprising following modules:

(1) an input module, which is used to input concentration of the miRNA combination of the sixth aspect of technical solution of the present disclosure contained in a sample to be tested; preferably, the sample to be tested is from a serum sample;

(2) an analysis module, which is used to calculate $LC_{score}$, wherein the $LC_{score}=0.5409+(\beta_1\times C_1+\ldots+\beta_n\times C_n)$, C represents concentration of miRNA, n represents number of miRNA, and β represents weighted assignment corresponding to the number of the miRNA, whose value ranges from 1 to 20, preferably 1 or an even number from 2 to 20; the number and weight of miRNAs are shown in the following table:

| Number (n) | miRNA | Weighted assignment (β) |
|---|---|---|
| 1 | miR-191 | +0.3350 |
| 2 | miR-454 | −0.4206 |
| 3 | miR-1285 | −0.2034 |
| 4 | miR-126 | +0.3019 |
| 5 | miR-181a-2* | +0.1077 |
| 6 | miR-203a | −0.1861 |
| 7 | miR-15b | −0.460 |
| 8 | miR-21 | +0.2339 |
| 9 | miR-365 | −0.0582 |
| 10 | miR-486-5p | +0.2970 |
| 11 | miR-375 | −0.2875 |
| 12 | miR-429 | −0.1120 |
| 13 | miR-141 | +0.0666 |
| 14 | miR-193b | +0.1581 |
| 15 | miR-125b | −0.1142 |
| 16 | miR-206 | −0.0656 |
| 17 | miR-155 | +0.0821 |
| 18 | miR-574-5p | +0.0706 |
| 19 | miR-19a | +0.2011 |
| 20 | miR-200b | +0.0459 |

For example, when n is 2, then the analysis module calculates a sum of weighted assignments and concentration products of miRNAs numbered 1 and 2, namely miR-191 and miR-454, to obtain $LC_{score}=0.5409+\beta_1\times C_1+\beta_2\times C_2=0.5409+0.3350\times C_{miR\text{-}191}-0.4206\times C_{miR\text{-}454}$.

When n is 4, then the analysis module calculates a sum of weighted assignments and concentration products of four miRNAs numbered 1 to 4, to obtain $LC_{score}=0.5409+\beta_1\times C_1+\beta_2\times C_2+\beta_3\times C_3+\beta_4\times C_4=0.5409+0.3350\times C_{miR\text{-}191}-0.4206\times C_{miR\text{-}454}-0.2034\times C_{miR\text{-}1285}+0.3019\times C_{miR\text{-}126}$. And so forth.

In a preferred specific embodiment, n is 20, and the analysis module calculates a sum of weighted assignments and concentration products of 20 miRNAs, to obtain $LC_{score}=0.5409-0.1142\times C_{miR\text{-}125b}+0.3019\times C_{miR\text{-}126}-0.2034\times C_{miR\text{-}1285}+0.0666\times C_{miR\text{-}141}+0.0821\times C_{miR\text{-}155}-0.460\times C_{miR\text{-}15b}+0.1077\times C_{miR\text{-}181a\text{-}2*}+0.3350\times C_{miR\text{-}191}+0.1581\times C_{miR\text{-}193b}+0.2011\times C_{miR\text{-}19a}+0.0459\times C_{miR\text{-}200b}-0.1861\times C_{miR\text{-}203a}-0.0656\times C_{miR\text{-}206}+0.2339\times C_{miR\text{-}21}-0.0582\times C_{miR\text{-}365}-0.2875\times C_{miR\text{-}375}-0.1120\times C_{miR\text{-}429}-0.4206\times C_{miR\text{-}454}+0.2970\times C_{miR\text{-}486\text{-}5p}+0.0706\times C_{miR\text{-}574\text{-}5p}$;

preferably, the lung cancer diagnosis system further comprises (3) a judgment module, when $LC_{score}\geq 0.5$, then the sample to be tested is judged as lung cancer; and when $LC_{score}<0.5$, then the sample to be tested is judged as health.

In some preferred embodiments, the lung cancer diagnosis system further comprises a printing module, which can print results generated by the input module, the analysis module, and the judgment module.

In some more preferred embodiments, in the input module, information of the miRNA is obtained by following steps:

(1) hybridizing a DNA probe with the miRNA, then adding an RNase H mutant conjugate, detecting fluorescent signal of a luminescent functional group, and calculating the concentration of the miRNA according to a standard curve; or, (2) adding a DNA probe, the miRNA, and an RNase H mutant conjugate simultaneously, detecting fluorescent signal of a luminescent functional group, and calculating the concentration of the miRNA according to a standard curve;

the RNase H mutant conjugate is RNase Hv-(Gly-Gly-Cys-$AF_{532}$)$_3$, wherein RNase Hv is an RNase H mutant, $AF_{532}$ is a luminescent functional group. Preferably, the RNase Hv has an amino acid sequence as shown in SEQ ID NO: 21.

In some preferred embodiments, the lung cancer diagnosis system further combines detection results of CEA, NSE, CYF21-1, SCC, CA125, CA199, and/or other lung cancer early diagnosis kits to determine whether the sample is from a lung cancer patient.

In order to solve the above technical problems, the tenth aspect of the technical solution of the present disclosure is to provide a computer-readable medium, wherein, the computer-readable medium stores a computer program, the computer program, being executed by a processor, can realize function of the lung cancer diagnosis system of the ninth aspect of the technical solution of the present disclosure.

In order to solve the above technical problems, the eleventh aspect of the technical solution of the present disclosure is to provide a detection device comprising a lung cancer diagnosis system, comprising:

(1) the computer-readable medium of the tenth aspect of the technical solution of the present disclosure;

(2) a processor for executing a computer program to realize function of the lung cancer diagnosis system.

In order to solve the above technical problems, the twelfth aspect of the technical solution of the present disclosure is to provide a use of the miRNA combination of the sixth aspect of the technical solution of the present disclosure in preparing a diagnostic reagent for detecting lung cancer or in screening a medicament for treating lung cancer; the lung cancer is preferably an early-stage lung cancer.

In order to solve the above technical problems, the thirteenth aspect of the technical solution of the present disclosure is to provide a method for lung cancer diagnosis, comprising following steps:

(1) obtaining concentration of the miRNA combination of the sixth aspect of the technical solution of the present disclosure contained in a sample to be tested; preferably, the sample to be tested is from a serum sample;

(2) calculating $LC_{score}$ according to a formula, wherein $LC_{score}=0.5409+(\beta_1\times C_1+\ .\ .\ .\ +\beta_n\times C_n)$, preferably, $LC_{score}=0.5409-0.1142\times C_{miR\text{-}125b}+0.3019\times C_{miR\text{-}126}-0.2034\times C_{miR\text{-}1285}+0.0666\times C_{miR\text{-}141}+0.0821\times C_{miR\text{-}155}-0.460\times C_{miR\text{-}15b}+0.1077\times C_{miR\text{-}181a\text{-}2*}+0.3350\times C_{miR\text{-}191}+0.1581\times C_{miR\text{-}193b}+0.2011\times C_{miR\text{-}19a}+0.0459\times C_{miR\text{-}200b}-0.1861\times C_{miR\text{-}203a}-0.0656\times C_{miR\text{-}206}+0.2339\times C_{miR\text{-}21}-0.0582\times C_{miR\text{-}365}-0.2875\times C_{miR\text{-}375}-0.1120\times C_{miR\text{-}429}-0.4206\times C_{miR\text{-}454}+0.2970\times C_{miR\text{-}486\text{-}5p}+0.0706\times C_{miR\text{-}574\text{-}5p}$;

(3) judging the sample to be tested as lung cancer when $LC_{score}\geq 0.5$; and judging the sample to be tested as health when $LC_{score}<0.5$.

On the basis of conforming to common knowledge in the art, the above-mentioned preferred conditions can be arbitrarily combined to obtain the preferred embodiments of the present disclosure.

The reagents and raw materials used in the present disclosure are all commercially available.

The positive progressive effects of the present disclosure are:

I. A Fluorescent Cross-Linked RNase H Mutant Conjugate and an Application Thereof:

1. A single-tube reaction realizes the detection of multiplex RNA. The single-tube reaction may simultaneously analyze multiple different target RNA molecules in the same sample. The detected throughput is equal to the number of types of microspheres, currently up to 500 types.

2. Without PCR amplification. Detection results are more accurate and false negatives are decreased in detection results.
3. Analysis of miRNAs biomarkers can be performed on various body fluids including blood, saliva, and urine.
4. Low sample consumption and high sensitivity: since 500 different RNA molecules can be detected simultaneously in the same reaction well, the sample consumption is greatly saved; samples with concentrations as low as nM can be detected, which can meet the needs of most biological detection.
5. Rapidness: due to the liquid phase system, the reaction time is greatly shortened, and the multiplex RNA molecule detection can be completed within 30 minutes.
6. Low cost: simultaneous detection of multiple indicators of a sample can save time, samples, reagents, consumables and labor, reduce detection costs, and improve analysis efficiency.
7. Flexibility: users only need to increase or decrease the microspheres with probes to meet the needs of different detecting projects;
8. Universality: various RNAs with different lengths (15–200 nt) can be detected, such as miRNAs, especially short miRNAs, without miRNA ligation or labeling.

II: A miRNA Combination and an Application Thereof

1. A method for effectively screening miRNAs associated with the diagnosis of diseases such as cancer, especially early-stage lung cancer, is provided.
2. Through mathematical modeling, a comprehensive judgment of multiple indicators is made to improve the analytical performance of a single biomarker indicator.
3. A miRNA biomarker and a combination thereof that can diagnose cancer, especially early stage lung cancer.
4. Non-invasive blood detection can effectively diagnose lung cancer in stages of T1N0M0 with a maximum diameter of 6 mm without puncture.
5. Rapid detection: only 120 minutes are taken from blood extraction to obtain detection results.
6. Low cost: simultaneous detection of multiple indicators of a sample can save time, samples, reagents, consumables, and labor, reduce testing costs, and improve analysis efficiency.
7. Universality: users only need to use different sequence probes to meet the needs of different disease detection projects;
8. The differentially expressed miRNAs obtained from large samples can be used as targets for drug screening.

BRIEF DESCRIPTION OF THE DRAWINGS

FIG. 2A is a fluorescence detection of 12% SDS-PAGE before staining; FIG. 2B is 12% SDS-PAGE stained by Coomassie brilliant blue G250; FIG. 2C is direct fluorescence detection of a dilution solution;

FIG. 4 shows the detection signal and sensitivity of miRNA let7a;

Figure 9:
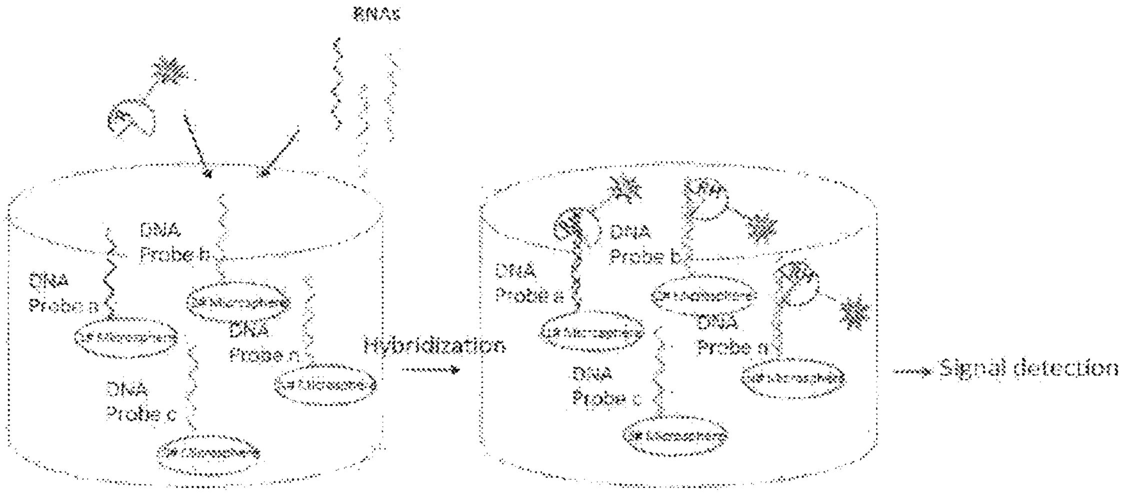
FIG. 9 is a schematic diagram of the principle of single-tube simultaneous detection of multiplex miRNA.

In the FIG. 9 is an electronic device, 91 is a processor, 92 is a memory, 93 is a bus, 94 is an external device, 95 is an I/O interface, and 96 is a network adapter;

921 is an RAM, 922 is a high-speed cache memory, 923 is an ROM, 924 is a program module, and 925 is a utility tool.

DETAILED DESCRIPTION OF THE PREFERRED EMBODIMENT

The present disclosure is further described below by means of embodiments, but the present disclosure is not limited to the scope of the described embodiments. The experimental methods that do not specify specific conditions in the following embodiments are selected according to conventional methods and conditions, or according to the product description.

TABLE 1

Construction and modification of RNase H protein and mutants thereof

| Protein ID | Content of protein construct (N terminal→ C terminal) | Abbreviation of protein | Abbreviation after AF532 modification |
|---|---|---|---|
| 1 | RNase H-$(His)_6$ | / | / |
| 2 | RNase H(E48Q)-$(His)_6$ | RHv | / |
| 3 | (Gly-Gly-Cys)- RHv-$(His)_6$ | RH1C | RH1CF |

TABLE 1-continued

Construction and modification of RNase H protein and mutants thereof

| Protein ID | Content of protein construct (N terminal→ C terminal) | Abbreviation of protein | Abbreviation after AF532 modification |
|---|---|---|---|
| 4 | RHv-(Gly-Gly-Cys)$_3$-(His)$_6$ | RH3C/<br>RH3C(GG) | RH3CF/<br>RH3CF(GG) |
| 5 | RHv-(Gly-Gly-Cys)$_5$-(His)$_6$ | RH5C | RH5CF |
| 6 | RHv-(Gly-Gly-Cys)$_7$-(His)$_6$ | RH7C | RH7CF |
| 7 | RHv-(Gly-Cys)$_3$-(His)$_6$ | RH3C (G) | RH3CF(G) |
| 8 | RHv-(Ala-Gly-Cys)$_3$-(His)$_6$ | RH3C(AG) | RH3CF(AG) |
| 9 | RHv-r(Gly)$_3$-Cysl$_3$-(His)$_6$ | RH3C(GGG) | RH3CF(GGG) |

In the above table, the subscripts of the Arabic numerals after the parentheses represent the number of groups or amino acid residues, for example (Gly)$_3$ represents three consecutive Glys, that is, the structure of Gly-Gly-Gly.

Embodiment 1 Construction of 9 *E. coli* RNase H and Plasmids Carrying Specific Molecularly Engineered Mutants 1. Construction of a Plasmid Expressing *E. coli* RNase H The genomic DNA of *E. coli* K12 was extracted. A 50 μL PCR reaction system containing 100 ng of genomic DNA of *E. coli* K12, 5 μL of 10×PCR buffer, 4 μL of dNTP mixture (2.5 mM each), 0.5 μL of each of 100 μM forward primer and reverse primer, 0.5 μL of pfx50 DNA polymerase (5 μ/L), added with sterile deionized water to 50 μL, was used for PCR amplification. The PCR reaction conditions were as follows: 94° C. for 2 min; 30 cycles of: 94° C. for 30 sec, 60° C. for 40 sec, and 68° C. for 3 min; finally 68° C. for 5 min.

The amplified PCR product was treated with a PCR product purification kit of Promega Company, and the purified PCR product that is finally obtained was reacted with a cloning vector pET33b using restriction enzymes Nco I and Xho I respectively at 37° C. for two hours, and then separated by 1% Agarose DNA electrophoresis. The target fragment was collected. The pET33b and PCR product after the action of restriction enzymes were ligated by T4 DNA ligase, and then transformed into DH5α competent cells. A transformation solution was spread on a kanamycin LB solid medium, and cultured upside down overnight at 37° C. A resistant monoclone was picked the next day and placed in a LB liquid medium containing kanamycin, inocubated overnight at 37° C., 200 r/min, and then sent to the sequencing company for sequence verification. An expression plasmid pET33b-rh was obtained, which is capable of expressing RNase H with a His purification tag (Protein ID: 1).

2. Construction of an RNase H(E48Q) Mutant with E48Q Mutation

Figure 1A:
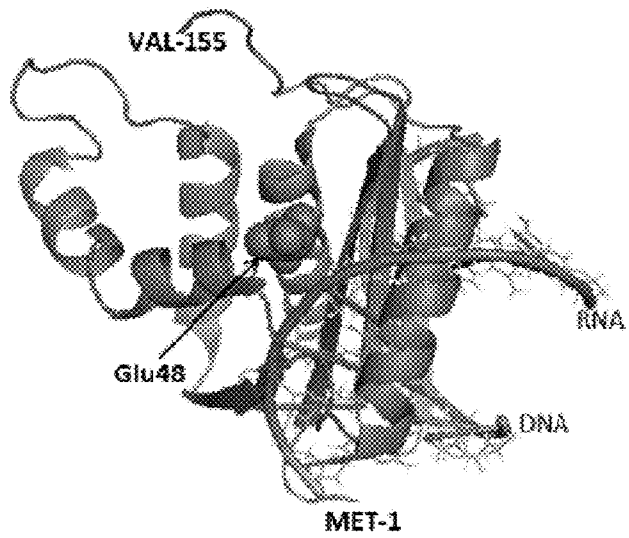
FIGS. 1A-1B respectively show a structure of RNase H binding to a RNA:DNA hybrid strand substrate and a hydrolysis mechanism thereof.
Figure 1B:
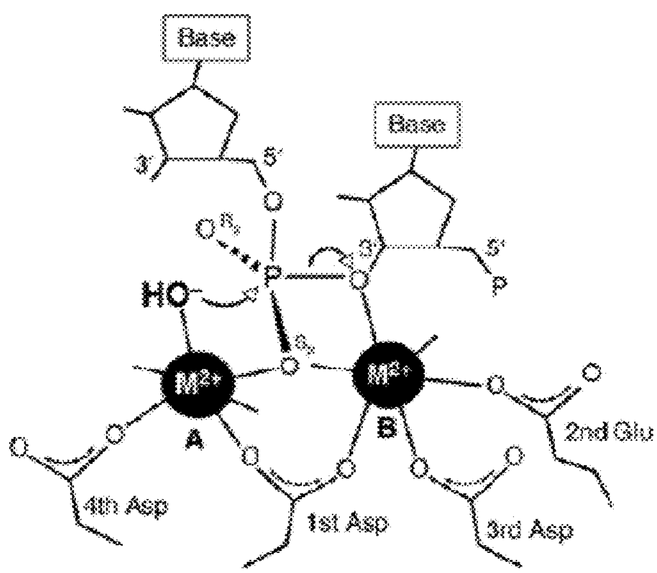

FIGS. 1A-1B respectively show a structure of RNase H binding to a RNA:DNA hybrid strand substrate and a hydrolysis mechanism thereof. On the pET33b-rh plasmid vector, the method of site-directed mutagenesis was used to convert 48Glu into 48Gln, so as to complete the transformation of the E48Q mutant and obtain pET33b-rh(E48Q) with the E48Q mutation. The specific experimental steps are as follows.

PCR amplification: a pair of reverse complementary primers which was point mutated at the mutation site were synthesized. A 50 μL PCR reaction system containing 0.5 μL of pET33-rh plasmid (about 50 ng), 5 μL of 10× buffer, 4 μL of dNTP mixture (2.5 mmol/L each), 2.0 μL of each of 100 μM forward primer and reverse primer, 0.5 μL of pfx50 DNA polymerase (5 μ/L), added with sterile deionized water to 50 μL, was used for PCR amplification. PCR reaction conditions: 94° C. for 30 sec; 18 cycles of: 94° C. for 30 sec, 60° C. for 40 sec, and 68° C. for 3 min; finally 68° C. for 5 min.

Digestion of the original template by Dpn I: 1 μL of Dpn I was added to 10 μL of PCR product, and incubated at 37° C. for 2 h. The original template plasmid was digested and cleaved.

Transforming into DH5a competent cells: according to the instructions of *E. coli* competent cells, 3 μL of PCR product from the digested original template plasmid was transformed into *E. coli* DH5a, the transformation solution was spread on a kanamycin LB solid medium, and cultured upside down overnight at 37° C. A resistant monoclone was picked the next day and placed in a LB liquid medium containing kanamycin, incubated overnight at 37° C., 200 r/min, and then sent to a sequencing company for sequencing. pET33b-rh(E48Q) was obtained.

3. Construction of RHv Mutants Carrying Various Numbers of Cys and Linkers from the E48Q Mutant (RHv)

According to the method of the above 2, combined with the technology improved by the present inventors previously (Wang et al., Molecular and Cellular Probes, 2010, 24: 15-19), starting from the plasmid expressing RNase H (E48Q), the expression plasmids of RHv mutants with 1 cysteine added at the N-terminal of the corresponding protein of RNase H (E48Q) and 3, 5, and 7 cysteines added before His-tag at the C-terminal of the corresponding protein of RNase H (E48Q) were successively constructed. The expressed proteins were obtained as RH1CF (Protein ID: 3), RH3CF/RH3CF(GG) (Protein ID: 4), RH5CF (Protein ID: 5) and RH7CF(G) (Protein ID: 6) respectively.

Similarly, starting from the plasmid expressing RNase H (E48Q), the expression plasmid of RHv mutants that have different linkers in types and lengths at the C-terminal of the protein were constructed. The protein structures in Table 1 can be expressed and obtained as RH3C(G) (Protein ID: 7), RH3C (AG) (Protein ID: 8), RH3C (GGG) (Protein ID: 9).

Figure 2:
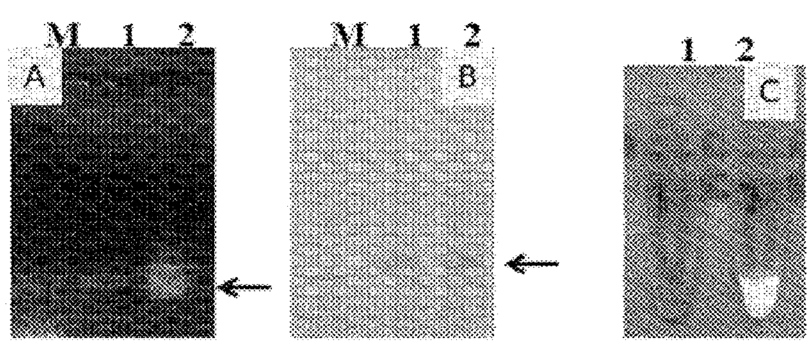
FIG. 2A, FIG. 2B, and FIG. 2C show a SDS-PAGE detection of RNase H expression, wherein M is a protein marker, lane 1 is RH3C (RNase H(E48Q)-3C), and lane 2 is RH3CF (RNase H(E48Q)-3 (Alexa Fluor A532))

Embodiment 2 Expression and Purification of Proteins (Protein ID 3-9) Carrying Seven Different Constructs Derived from RNase H Mutant RHv Taking pET33b-rh(E48Q)-3C (Protein ID: 3) as an example, a pET33b-rh(E48Q)-3Cys plasmid was transformed into *E. coli* Bl21(DE3) for protein expression. The transformation solution was inoculated and cultured until the OD600 reading value reached about 0.6, added with an inducer IPTG (isopropyl thiogalactoside, Isopropyl β-D-Thiogalactoside) to a final concentration of 1.0 mM to induce the expression of a target protein, and the bacteria cells were collected by centrifugation after induction for 4 hours. The bacterial cells were disrupted by ultrasonication in PBS, the supernatant collected by centrifugation was bound to Ni-NTA resin, and then eluted with imidazole to obtain the target protein RNase H(E48Q)-3Cys (RH3C for short), which was dialyzed with PBS for later use (FIG. 2A, FIG. 2B, and FIG. 2C, wherein, FIG. 2A is a fluorescence detection of 12% SDS-PAGE before staining, FIG. 2B is 12% SDS-PAGE stained by Coomassie brilliant blue G250, and FIG. 2C is a direct fluorescence detection of dilution).

Embodiment 3 Fluorescent Substance Labeling and Purification of Seven Proteins (Protein ID 3-9) with Different Constructs Taking RH3C as an example, three cysteines brought onto C-terminal of RNase H protein by molecular modification were fluorescently labeled, so as to specifically obtain fluorescently labeled RNase H(E48Q)-(Alexa Fluor A532) 3, namely RH3CF.

RH3C was quantified by the Bradford method. 1 mg/mL RH3C was added into 1 mg/ml Alexa Fluor™ 532 C5 Maleimide (Cat. No: A10255, Thermo Fisher), and reacted at 30° C. for 1 hour in the dark. Centrifuged by a 10 kDa ultrafiltration tube three times, uncrosslinked free Alexa Fluor™ 532 C5 Maleimide was then removed. The obtained product was mainly RNase H(E48Q)-(Alexa Fluor 532) 3 (RH3CF for short) (FIG. 2A, FIG. 2B, and FIG. 2C).

Using the same method, seven fluorescent-modified conjugates of protein ID 3-9 carrying specific molecular modifications were obtained respectively.

Figure 3:
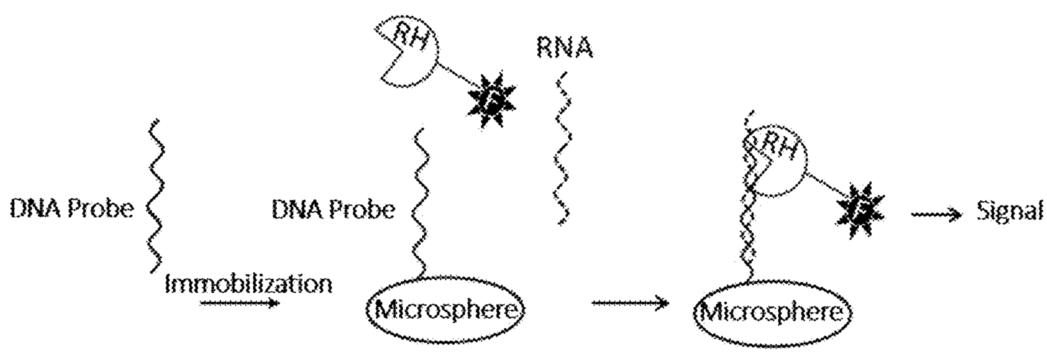
FIG. 3 shows a schematic diagram of a detection principle.

Embodiment 4 Covalent Cross-Linking Coating of Probes and Carboxylated Polystyrene Microspheres FIG. 3 is a schematic diagram of a detection principle of an immobilized DNA probe. The synthesized oligonucleotide DNA probes and RNA sequences are shown in Table 2. Herein, 3' ends of the probes shown in the sequences of SEQ ID NO: 1-14 contain NH2-C6 modification.

TABLE 2

Probes and modifications thereof and RNA sequences used for covalent cross-linking

| SEQ ID NO: | Name* | Sequence (5' → 3') | Sequence or modification |
|---|---|---|---|
| 1 | P3-let7a (P-let7a) | AACTATACAACCTACTACCTCATTTTTT | 3' NH2-C6 |
| 2 | P5-let7a | TTTTTTAACTATACAACCTACTACCTCA | 5' NH2-C6 |
| | P5-6A | AAAAAA | 5' NH2-C6 |
| 3 | P3-LNA-let7a | AAcTATACAACCtACTAcCTCATTTTTT | 3' NH2-C3 |
| 4 | P3-1a | GGAGTCTCCAAAGCCACGTACTTTTTT | 3' NH2-C6 |
| 5 | P-let7b | AACCACACAACCTACTACCTCATTTTTT | 3'NH2-C6 |
| 6 | P-m141 | CCATCTTTACCAGACAGTGTTATTTTTT | 3'NH2-C6 |
| 7 | P-m155 | ACCCCTATCACGATTAGCATTAATTTTTT | 3'NH2-C6 |
| 8 | P-m375 | TCACGCGAGCCGAACGAACAAATTTTTT | 3'NH2-C6 |
| 9 | P-RNU6 | CCAATTTTAGTATATGTGCTGCCGTTTTTT | 3'NH2-C6 |
| 10 | P-m34a | ACAACCAGCTAAGACACTGCCATTTTTT | 3'NH2-C6 |
| 11 | P-m16 | CGCCAATATTTACGTGCTGCTATTTTTT | 3'NH2-C6 |
| 12 | P-m151 | CCTCAAGGAGCTTCAGTCTAGTTTTTT | 3'NH2-C6 |
| 13 | P-m145 | AGGGATTCCTGGGAAAACTGGACTTTTTT | 3'NH2-C6 |
| 14 | let-7a | UGAGGUAGUAGGUUGUAUAGUU | RNA |
| 15 | m155 | UUAAUGCUAAUCGUGAUAGGGGU | RNA |
| 16 | m141 | UAACACUGUCUGGUAAAGAUGG | RNA |
| 17 | Rp | GGAAGACAATCTTCATCTCCTTCTG | DNA (no modification) |
| 18 | RCA-1a | AAGATTGTGTTGGGAAGGATGGATGGATGT TTAAGATGTTGAGGTGGGTGTGATAAGAGG TGGTGGAGGGAGTGTGGAAAGGGAGGTAGG TTAGTTTTTTTGGATGGATGGTTGTAATAG GAGTGAGTATAGGGAGAGAGAAGGAGATG | DNA (no modification) |
| 19 | 1a | GUACGUGGCUUUGGAGACUCCGUGGAGGAG GUCUUAUCAGAGGCACGUCAACAUCUUAAA GAUG | RNA |

TABLE 2-continued

| Probes and modifications thereof and RNA sequences used for covalent cross-linking | | | |
|---|---|---|---|
| SEQ ID NO: | Name* | Sequence (5' → 3') | Sequence or modification |
| 20 | E48Q | MLKQVEIFTDGSCLGNPGPGGYGAILRYRG REKTFSAGYTRTTNNRMQLMAAIVALEALK EHCEVILSTDSQYVRQGITQWIHNWKKRGW KTADKKPVKNVDLWQRLDAALGQHQIKWEW VKGHAGHPENERCDELARAAAMNPTLEDTG YQVEV | RNase Hv |

*In the DNA/LNA probes in Table 2, P3 represents that the 3' end of the detection probe is immobilized on a solid phase carrier, and P5 represents that the 5' end of the detection probe is immobilized on the solid phase carrier. Lowercase c and t represent LNA (Locked nucleic acid) modification.

Ten carboxylated polystyrene microspheres (Cat. Nos. LC10001-01, LC10001-02, LC10001-03, LC10001-04, LC10001-05, LC10001-06, LC10001-07, LC10001-08, LC10001-09, and LC10001-10, Luminex Company) were selected, and the covalent cross-linking coating of probes and microspheres was carried out according to the following method:

(1) The probes were dissolved in double distilled water to a concentration of 100 μM.

(2) Microsphere washing: 50 μL of each microsphere (containing $6.0\times10^5$ microspheres) was taken and centrifuged under the condition of 10000 g centrifugal force for 5 minutes to precipitate, and a supernatant was discarded. 50 μL of 0.1 M MES solution, pH 4.5, was then added thereto, and shaken for 15 sec to suspend the microspheres, centrifuged under the condition of 10000 g centrifugal force for 5 minutes to precipitate the microspheres, and the supernatant was discarded. The microspheres were resuspended with 50 μL of 0.1 M MES, pH 4.5.

(3) Covalently cross-linking probes and microspheres: 2.0 μL of 100 μM probe was added to the corresponding microsphere suspension of the previous step and mixed uniformly, 2.5 μL of 10 mg/mL EDC (3-(ethyliminomethylideneamino)-N,N-dimethylpropan-1-amine, hydrochloride) solution was added thereto, reacted at 37° C. for 30 min in the dark.

(4) 2.5 μL of 10 mg/mL EDC solution was added thereto again, reacted at 37° C. for 30 min in the dark.

(5) The mixture was centrifuged under the condition of 10000 g centrifugal force for 5 min to precipitate the microspheres. 1.0 mL of 0.1% SDS was added thereto to resuspend the microspheres, and mixed uniformly using a shaker, and centrifuged under the condition of 10000 g centrifugal force for 5 min to precipitate.

(6) The supernatant was discarded and the microspheres were resuspended with 100 μL of TE (pH 8.0).

Embodiment 5 Quantitative Detection Curve

1. An oligonucleotide DNA probe P3-let7a (SEQ ID NO: 1) and carboxylated polystyrene microspheres (Cat. No. LC10001-01, Luminex Company) were covalently cross-linked and coated according to the conditions in Embodiment 4.

2. miRNA detection (1) Standard: a synthetic miRNA let7a (SEQ ID NO: 14) was dissolved in TE to a final concentration of 10 μM, and then diluted to 50 nM, 20 nM, 10 nM, 500 μM, 200 μM, 100 μM, 50 μM, and 20 μM, respectively.

(2) Mixing: 2.0 μL volume of miRNA, 2.0 μL of a microsphere mixture, and 1.0 μL of RH3CF at concentration of 10 nM were added to 15.0 μL of a hybridization solution (500 mM NaCl, 0.05% TWEEN® 20 (polysorbate 20), 1 mM $MgCl_2$, 50 mM Tris-HCl, pH 7.5) and mixed uniformly by a vortex for 5 sec. The standard of miRNA let7a at each concentration was tested in 5 replicates.

(3) Hybridization reaction: placed in a pre-set 42° C. water bath for 20 min.

(4) Detection: 80 μL of hybridization diluent (100 mM NaCl, 0.05% TWEEN® 20, 20 mM Tris-HCl, pH 7.5) was added, pipetted into a 96-well plate, and put into Luminex-200 for detection.

Figure 4:
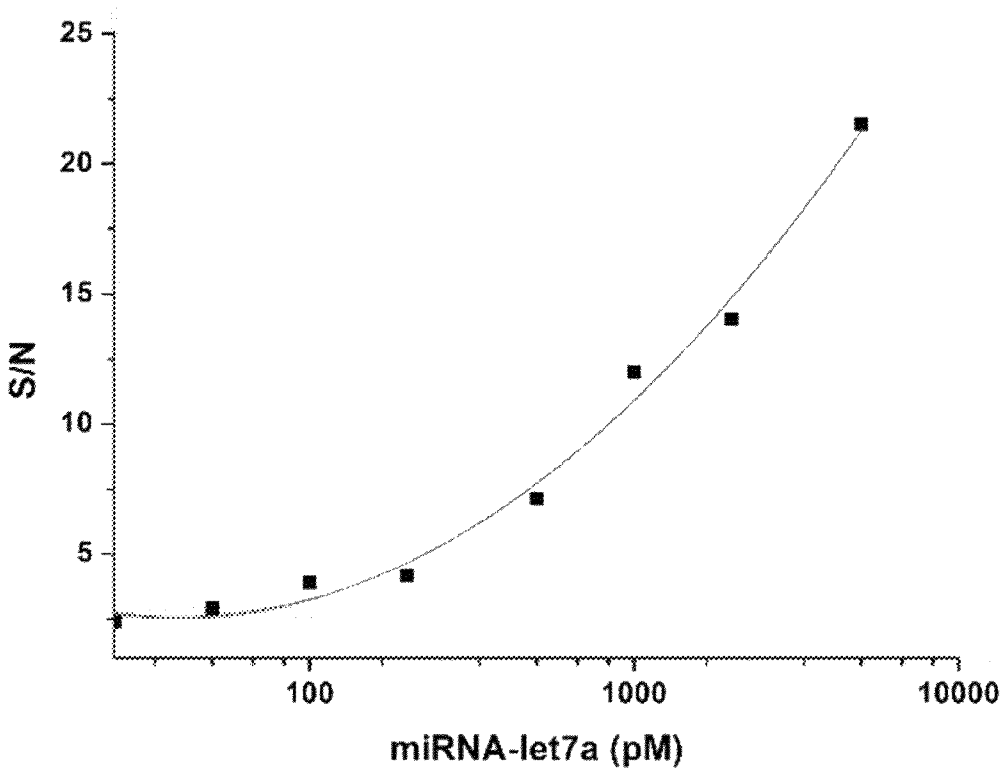

(5) Data analysis and fitting: as shown in FIG. 4.

The detection sensitivity was 5-10 μM of miRNA let7a in the reaction system.

Embodiment 6 Effects of Probe Combinations with Different Sequences, Types and Immobilizing Directions For the RH3CF prepared by the present disclosure, by recognizing a DNA/RNA hybrid formed by a detection probe immobilized on the surface of the carboxylated polystyrene microspheres (Cat. No. LC10001-01, Luminex Company) and a target RNA, a concentration-related fluorescence signal was obtained. Therefore, the immobilization of different types of probes (DNA and locked nucleic acid LNA, etc.) on a solid phase carrier and the different modifications on their surface can affect a non-specific signal noise, resulting in discrepant detection signals, which ultimately affects the minimum detection limit of the detection system. The present disclosure compares the different immobilizing directions of probes:

1) The difference in detection signals by immobilization at 5' and 3' ends of the DNA probes 2) Immobilization of DNA probes with the same sequence by different ratios of 5' and 3' ends 3) Immobilization of probes with the same sequence at 3' and 5' ends of the target probes 4) Immobilization of probes with different sequences and lengths at 3' and 5' ends of the target probes 5) Immobilization of DNA and LNA probes with the same sequence at 3' end The probes and modifications thereof used in this embodiment of the present disclosure are shown in Table 2.

In this embodiment, according to the ratio and volume in Table 3, carboxylated polystyrene microspheres in a volume of 50 μL were added to the probes of SEQ ID NO: 1-4 combination in 8 reaction tubes respectively, and mixed uniformly. 2.5 μL of 10 mg/mL EDC solution was added thereto and reacted at 37° C. for 30 min in the dark. 2.5 μL of 10 mg/mL EDC solution was added thereto again and reacted at 37° C. for 30 min in the dark. The mixture was centrifuged under the condition of 10,000 g centrifugal force for 5 min to precipitate microspheres. 1.0 mL of 0.1% SDS was added to resuspend the microspheres, mixed uniformly using a shaker, and centrifuged under the condition of 10,000 g centrifugal force for 5 min to precipitate the microspheres. Finally, the supernatant was discarded and the microspheres were resuspended with 100 μL of TE (pH 8.0). That is, microsphere detection probes with mixed modifications of different types of probes were obtained.

TABLE 3

Probe combinations of different sequences, types and immobilizing directions

| Number | Combination | Probe A | Probe B | Quantity of addition |
|---|---|---|---|---|
| 1 | DNA | 100% P3-let7a | | 2.0 μL 100 μM P3-let7a |
| 2 | DNA 80% | 80% P3-let7a | 20% P5-let7a | 1.6 μL 100 μM P3-let7a + 0.4 μL 100 μM P5-let7a |
| 3 | DNA 50% | 50% P3-let7a | 50% P5-let7a | 1.0 μL 100 μM P3-let7a + 1.0 μL 100 μM P5-let7a |
| 4 | DNA | | 100% P5-let7a | 2.0 μL 100 μM P5-let7a |
| 5 | DNA/6A | 80% P3-let7a | 20% P5-6A | 1.6 μL 100 μM P3-let7a + 0.4 μL 100 μMP5-6A |
| 6 | LNA | 100% P3-LNA-let7a | | 2.0 μL 100 μM P3-LNA-let7a |
| 7 | LNA/6A | 80% P3-LNA-let7a | 20% P5-6A | 1.6 μL 100 μM P3-LNA-let7a + 0.4 μL 100 μMP5-6A |
| 8 | DNA/LNA | 50% P3-let7a | 50% P3-LNA-let7a | 1.0 μL 100 μM P3-LNA-let7a + 1.0 μL 100 μM P3-let7a |

Figure 5:
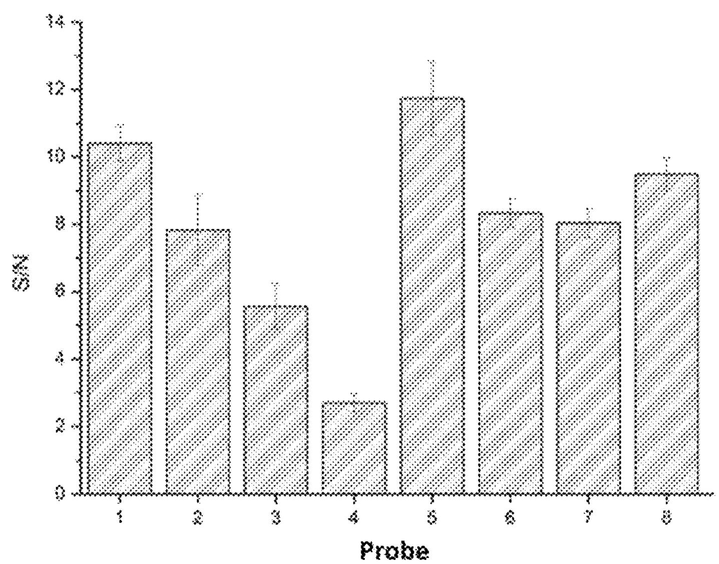
FIG. 5 shows the effects and results of probes with different sequences, types, ratios, and immobilizing directions on the detection signal.

The synthesized miRNA let7a was dissolved in TE and diluted to 10 nM. 2.0 L volume of miRNA, 2.0 μL of a microsphere mixture, and 1.0 μL of 1 μM RH3CF were added to 15.0 μL of a hybridization solution (500 mM NaCl, 0.05% TWEEN® 20, 1 mM $MgCl_2$, 50 mM Tris-HCl, pH 7.5), and mixed uniformly by a vortex for 5 sec. The mixture was placed in a pre-set 42° C. water bath for 20 min. 80 μL of hybridization dilution solution (100 mM NaCl, 0.05% TWEEN® 20, 20 mM Tris-HCl, pH 7.5) was added thereto, pipetted into a 96-well plate, and put into Luminex-200 for detection. Each combination was repeated three times, and the results were obtained as shown in FIG. 5. Herein, combinations 1, 5-8 have the highest signal-to-noise ratio (S/N). It can be seen that a certain proportion of non-target probe DNA sequences (e.g., P5-6A used in Table 3 above), simultaneously immobilized with the target probe sequences on the solid phase carrier (e.g., combinations 5 and 7), can not only control and optimize the density of probes on the solid phase carrier, but also achieve the modifications of the solid phase surface to reduce non-specific adsorption. Target probes with optimized density, such as P3-let7a in this embodiment, and surface modifications with sequences that are not complementary to the detection target RNA, can improve the detection signal while reducing the noise signal generated by non-specific adsorption, and finally achieve the purpose of improving the minimum detection limit. The reason why LNA probe does not show superior detection performance than the DNA probe in this embodiment may be that after LNA modification, the temperature required for complete hybridization needs to be increased by 4° C./nucleotide. Therefore, the temperature of reaction condition in this embodiment is not optimal for LNA. On the contrary, a certain proportion of LNA mixed with DNA can improve the detection performance of LNA probes (e.g., combination 6 compared with combination 8), which explains the need to optimize the optimal conditions for LNA probes from another aspect.

The present disclosure confirms and verifies for the first time that DNA/RNA recognition based on RNase H molecule has a definite directionality. Immobilization at 3' end of the probe, or keeping the 5' end of the probe that is recognized by RNA in a free and accessible state, is a necessary path for the binding and recognition of RNase H of the present disclosure and from other sources. By mixing probes with the same sequence but different immobilizing directions, the detection signal decreased gradually, and 100% of the probes immobilized at the 5' end had a signal-to-noise ratio of 1.2, verifying the contribution of the present disclosure.

Embodiment 7 Comparison of the Effects of Cross-Linked Conjugates of RNase H (E48Q) Carrying 1, 3, 5, or 7 of Cysteine that can be Site-Directed Covalently Cross Linked on the Detection Signals The cross-linked conjugates of RNase H(E48Q) carrying 1, 3, 5, and 7 cysteines that can be site-directed covalently cross-linked are RH1CF, RH3CF, RH5CF, and RH7CF, respectively.

The synthetic miRNAlet7a (SEQ ID NO: 14) was dissolved in TE and diluted to 10 nM. Under the same conditions as those in Embodiment 6, the P3-let7a probe microsphere of No. 1 (SEQ ID NO: 1) in Table 3 was selected, and a signal generated by the let7a miRNA at a final concentration of 1 nM was tested. Each combination was repeated three times, and the results were obtained as shown in FIG.

Figure 6:
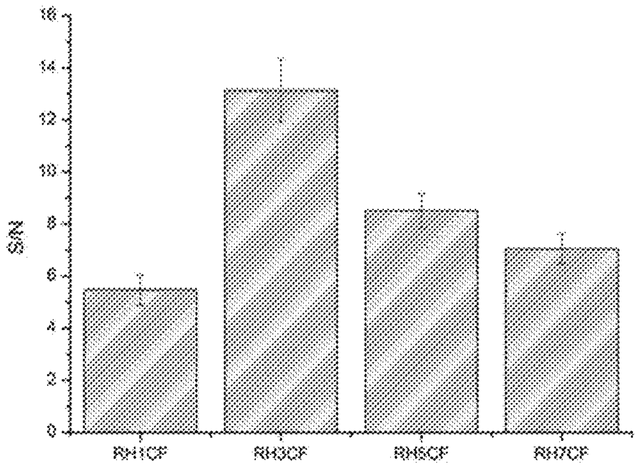
FIG. 6 shows the effects of cross-linked conjugates of RNase H (E48Q) carrying 1, 3, 5, or 7 of cysteines that can be site-directed covalently cross-linked respectively on the detection signal.

6. The optimal number of Cys carried at the end of a specifically modified molecule is 3, which can obtain the highest detection signal. *E. coli* RNase H itself carries three Cys amino acids, which are distributed in the inner/non-surface region of its higher-order structure and are not easily site-directed modified and cross-linked. FIG. 6 shows that a single Cys produces the lowest fluorescence signal, while multiple Cys, such as 5 and 7 Cys in this embodiment, theoretically bring in more fluorophores through more Cys, which can generate stronger fluorescence signal. However, too much fluorescent molecular modification may bring a certain degree of protein denaturation benefits to RNase H itself, resulting in a decrease in the binding ability of RNase H, so that the overall detection signal is not improved. Therefore, the molecular modification of RNase H in the present disclosure has shown the best balance, and 3 Cys can produce the best effect.

Embodiment 8 Effects of the Length and Type of a Linker Before the Cys at the End of RNase H (E48Q) on the Detection Signal For the RH3CF(G), RH3C/RH3C(GG), RH3CF(AG) and RH3CF(GGG) prepared in Table 1, four different combinations of cysteine linkers, $(Gly\text{-}Cys)_3$, $(Gly\text{-}Gly\text{-}Cys)_3$, $(Ala\text{-}Gly\text{-}Cys)_3$ and $([Gly]3\text{-}Cys)_3$, were added before the corresponding protein C-terminal His-tag of RNase H(E48Q), respectively, thereby obtaining four proteins of Protein ID 6-9.

Figure 7:
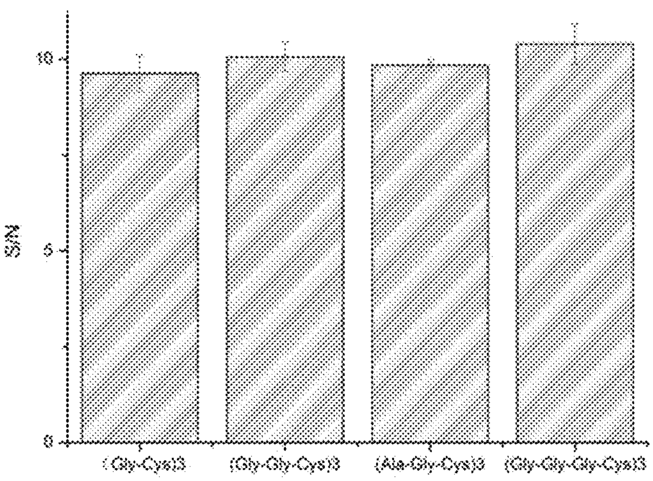
FIG. 7 shows the effects of RNase H (E48Q) carrying complexes with different linker amino acids respectively on the detection signal.

10 nM miRNA let7a was tested according to the conditions of Embodiment 7, and each combination was repeated three times, and the results were obtained as shown in FIG. 7 below. The purpose of adding a non-polar linker is to maintain a distance between two adjacent cysteines that can be covalently cross-linked by fluorescence, to reduce steric hindrance, and to improve the effect of covalently cross-linked fluorescent groups. Therefore, 1-3 amino acids were selected as linkers for testing, and the detection results showed that the combination of four different linkers exhibiting no obvious difference, and the effect of 3 consecutive Gly as a linker is the best, slightly better than the detection signal generated by the 2-Gly linker. From the benefits of 1-3 linkers, 3-Gly linker can generate the best detection signal. Partially replaced Gly with Ala has limited effect on results. In order to increase the steric distance and structure between the two cysteines and improve the cross-linking efficiency with the fluorophore, it is required to reduce the steric hindrance effect through the connection of non-polar amino acids. Glycine does not form a three-dimensional chemical structure due to a side chain group, lacks beta carbon atoms as well, and forms a more flexible peptide chain, therefore it can provide more spatial structure, and at the same time has the least effect on the chemical activity of the vicinal amino acid, so glycine becomes the preferred linker amino acid in the technology of the present disclosure. Among the known amino acids, the side chain group of alanine is inferior only to glycine in terms of steric hindrance and hydrophobicity, and has weak hydrophobicity, which can form a weakly hydrophobic environment conducive to the intervention of hydrophobic fluorescent groups. Therefore, both are the preferred linking amino acids in preparing site-specific molecular modifications and maintaining the biological activity of the target molecule. The linkers of three or four consecutive non-polar amino acids in this embodiment have no significant difference in the finally generated signals, which also reflects the need for a reasonable balance among the spatial distance, the flexibility and the hydrophobicity of the linker amino acids.

Embodiment 9 Effects of Conjugates Covalently Cross-Linked by AF532/AF555 and RH3C/RH7C in Different Fluorescence Bands on Detection Signals Covalent cross-linking: 1 mg/mL RH3C and RH7C respectively cross-linked with 1 mg/mL Alexa Fluor™ 555 C2 Maleimide (Cat. No.: A20346, Thermo Fisher) and purified, according to the conditions in Embodiment 3. Alexa Fluor 555-labeled RH3CF555 and RH7CF555 were obtained.

Figure 8:
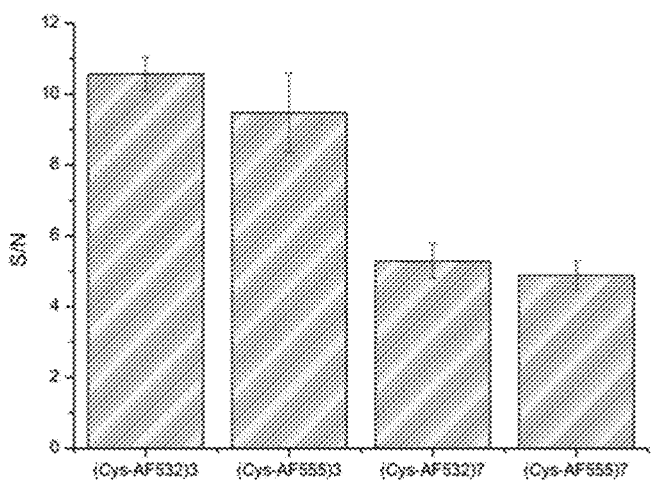
FIG. 8 shows the effects of conjugates of RNaseH(E48Q)-3C covalently cross-linked with AF532 and AF555 in different fluorescence bands on detection signal.

Signal detection: 10 nM miRNA let7a was tested according to the conditions of Embodiment 7, RH3CF and RH7CF (fluorescently labeled AF532), RH3CF555 and RH7CF555 were compared. Each combination was repeated three times, and the results were obtained as shown in FIG. 8 below. The detection signal of AF532-labeled RH3CF with the same concentration of miRNA was the highest, and the detection signal of AF555-labeled RH3CF555 was 90% of the former. Similar results were obtained when RH7C was labeled by AF532 and AF555, respectively. Therefore, in this embodiment, RH3CF is the preferred combination, followed by RH3CF555. This embodiment and Embodiment 7 once again verify that in order to achieve the best signal conversion and molecular recognition, this specifically modified molecule has a certain degree of optimization of the optimal amount of exogenously added cysteine, and excessive fluorescent molecule modification has an impact on the binding and recognition activity of RNase H, which may be due to a certain degree of protein denaturation, leading to a decrease in the binding ability of RNase H, thereby reducing the overall detection signal.

Embodiment 10 Detection of Transcriptionally Synthesized RNA 1a (SEQ ID NO: 9) with a Length of 64 Nucleotides A 5' end phosphorylated DNA RCA-1a (SEQ ID NO: 18) was synthesized. The design was based on the padlock principle of rolling circle amplification (Deng et al., Chem. Sci. 2017, 8(5), 3668-3675), which can generate RNA with a length of 64 oligonucleotides, the sequence was derived from ORF 1a of Covid-19. A linear padlock probe RCA-1a-p was first phosphorylated in a volume of 20 μL. 2 μL of 100 μM linear probe, 2 μL of 10×T4 polynucleotide kinase reaction buffer, 15.5 μL of DEPC-treated $H_2O$, and 0.5 μL of T4 polynucleotide kinase (10 μ/L) were added. 4 μL of phosphorylated padlock probe (100 nM), 4 μL of 10×T4 DNA ligase reaction buffer, 4 μL of Rp (SEQ ID NO: 17) target DNA solution (1 μM), 27.5 μL of DEPC-treated $H_2O$, and 0.5 μL of 5μ/L T4 DNA ligase were added to the ligation reaction. The reaction mixture was heated at 55° C. for 5 minutes before the addition of T4 DNA ligase, and then annealed at 39° C. for 30 minutes and cooled to room temperature, T4 DNA ligase was added thereto and the ligation reaction was carried out at 30° C. for 30 minutes. The product of the ligation reaction was added to an RCA reaction mixture containing 5 μL of 10×phi29 DNA polymerase reaction buffer, 4 μL of dNTPs (10 mM each of dATP, dGTP, dCTP, and dTTP), 0.5 μL of DEPC-treated $H_2O$, and 0.5 μL of phi29 DNA polymerase (10 μ/L). The RCA reaction was carried out at 37° C. for 2 h, and the reaction was terminated by incubation at 65° C. for 10 min. Negative controls were reactions without the addition of phi29 DNA polymerase.

Signal detection: 2.0 μL of negative control, P3-1a (SEQ ID NO: 5) cross-linked probe microspheres, 1.0 μL of RH3CF at a concentration of 1 μM, and 15.0 μL of hybridization solution were added to 0.2, 0.5, and 2.0 μL volumes of ORF 1a RNA with a length of 64 nucleotides synthesized by rolling circle reaction respectively and mixed uniformly, incubated at 45° C. for 20 minutes, and pipetted into a 96-well plate and put into Luminex-200 for detection. S/N values of signal of negative controls, and the addition of 0.2, 0.5, and 2.0 μL were read as 1.12, 4.81, 8.22, and 12.10, respectively. According to the standard curve for let7a in Embodiment 4, the concentrations of the corresponding detected synthetic target RNA were −0.10, 0.26, 0.62 and 1.0 nM, respectively. The detected signal of the negative control is significantly different from that of the addition of different amounts of 1*a* RNA, indicating that the technology of the present disclosure, in addition to detecting miRNAs with a length of 19-25 nucleotides, can qualitatively detect RNAs of other lengths. From the principle of molecular biology, as long as the probe DNA and a part of the specific sequence region of the target RNA can perform double-strand complementary hybridization recognition, it can detect them all. Therefore, the technology of the present disclosure has universal applicability to the qualitative detection of RNAs of different lengths.

Embodiment 11 Specificity of Multiplex miRNA Simultaneous Detection

The specificity of multiplex miRNA simultaneous detection depends on the system's ability to discriminate the base changes at one or several sites of RNAs with similar sequences (mismatch discrimination). miRNA let7a and let7b have two-base difference near the 3' end (FIG. 10A), and probes P-let7a (SEQ ID NO: 1) and P-let7b (SEQ ID NO: 2), which are completely complementary to let7a and let7b, were used respectively to detect the recognition ability of mismatch.

Figure 10A:
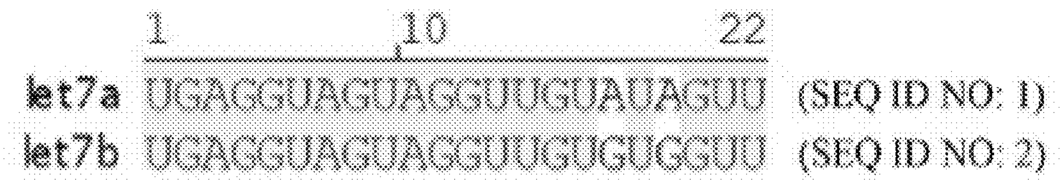
FIGS. 10A-10B show the detection of the specificity of a miRNA mismatched base.
Figure 10B:
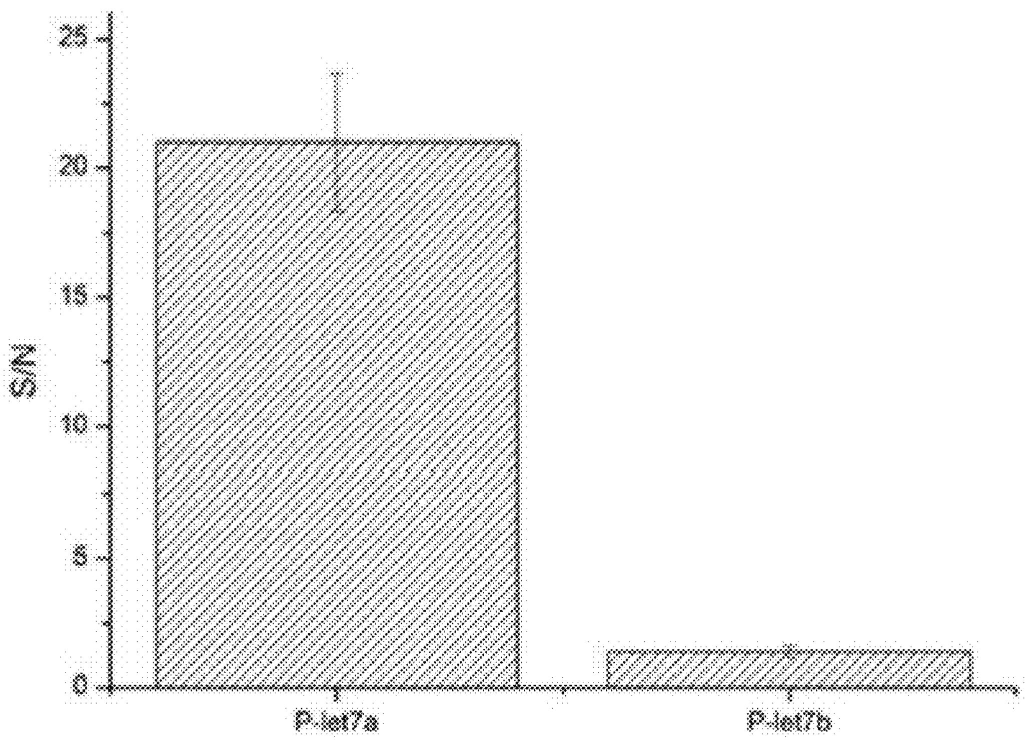

A volume of 2.0 μL of 10 nM let7a (SEQ ID NO: 14), 2.0 μL of P-let7a (SEQ ID NO: 1 cross-linked with Luminex microsphere LC10001-01) and P-let7b (SEQ ID NO: 6 cross-linked with Luminex microsphere LC10001-02) microsphere mixture, 1.0 L of RH3CF at the concentration of 10 nM, were added to 15.0 μL hybridization solution and mixed uniformly. The mixture was reacted at 42° C. for 20 minutes, then 80 L of hybridization dilution was added thereto, and transferred to a 96-well plate, and put into Luminex-200 to detect the fluorescent signal. The statistics of the five detection results are shown in FIGS. 10A-10B, respectively, and S/N (signal-to-noise) ratio represents the intensity of detected fluorescence. The P-let7b probe and the let7a sequence have two mismatched bases, located in the middle of the RNA near the 3' end, and the detection signal is about 5-8% of the fully complementary P-let7a (FIG. 10B). It can be seen that, the multiplex detection system constructed by the present disclosure has high specificity in detection even with similar RNA sequences such as let7a and let7b.

Embodiment 12 Single-Tube Simultaneous Detection of Two Kinds of miRNAs miR-141 and miR-155

Figure 11:
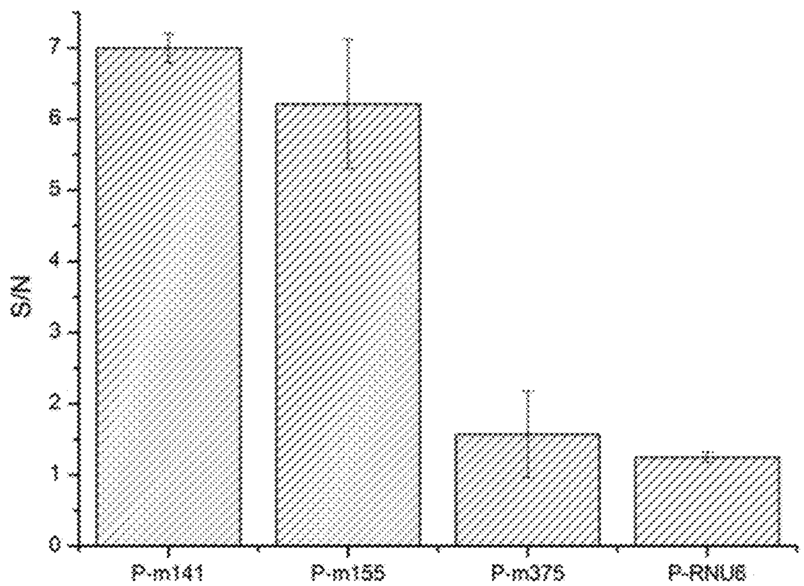
FIG. 11 shows the results of simultaneous detection of two kinds of miRNAs in a single-tube reaction.

The synthesized miRNAs m155 (SEQ ID NO: 15) and m141 (SEQ ID NO: 16) were respectively dissolved in TE to a final concentration of 10 μM, then mixed at a ratio of 1:1 and diluted to 10 nM. 2.0 μL of a mixed solution of m141 and m155, 2.0 μL of mixed microsphere solution containing P-m141 (SEQ ID NO: 6 cross-linked with Luminex microsphere LC10001-03) and P-m155 (SEQ ID NO: 7 cross-linked with Luminex microsphere LC10001-03), P-m375 (SEQ ID NO: 8 cross-linked with Luminex microsphere LC10001-03) and P-RNU6 (SEQ ID NO: 9 cross-linked with Luminex microspheres LC10001-03), 1.0 μL of RH3CF at a concentration of 10 nM were added to 15.0 μL of hybridization solution and mixed uniformly. The mixture was reacted at 42° C. for 20 minutes, 80 μL of hybridization dilution was added thereto, transferred to a 96-well plate, and put into Luminex-200 to detect the fluorescent signal. The statistics of the five detection results are shown in FIG. 11, miR-141 and miR-155 generated specific signals at the corresponding probes P-m141 and P-m155. Probes P-m375 and P-RNU6, which are not directly related to the target miRNA sequence, also showed 10-15% of signal values, because multiplex probes have inevitable crossover to a certain extent, although it does not affect the results of multiplex detection.

Embodiment 13 Detection of miRNA miR-34a in Blood

Figure 12:
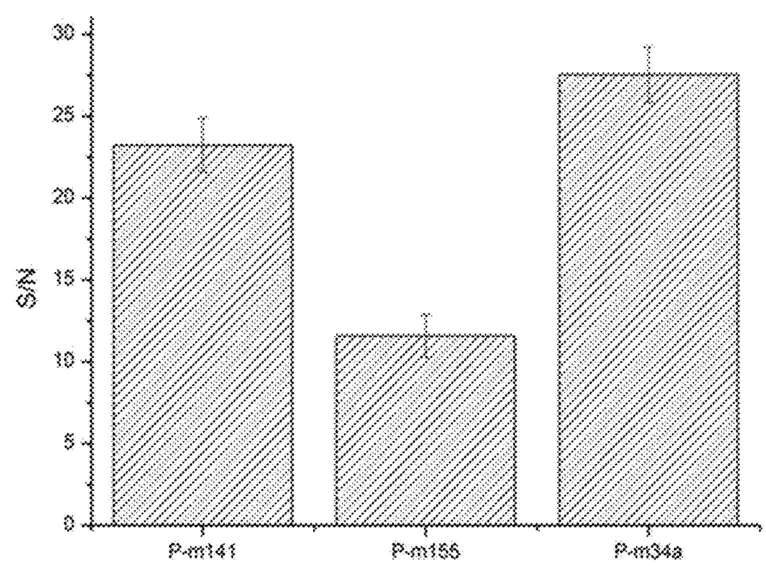
FIG. 12 shows the results of simultaneous detection of blood-derived miR-34a in a single-tube reaction.

The advantage of multiplex miRNA single-tube simultaneous detection without PCR amplification is that the content information of multiple target miRNAs can be obtained simultaneously in one reaction tube, avoiding PCR inhibitors, CG content and other factors in the process of RT-PCR amplification detection that lead to bias in ligation or labeling and eventually result in false negative test results. The present disclosure takes the detection of miR-34a in blood as an example for comparison. Some foreign research reports showed that the content of miR-34a in blood is low and cannot be detected, so miR-34a was added as an external reference (Optimization and Standardization of Circulating MicroRNA Detection for Clinical Application The miR-Test Case, Clinical Chemistry, 2016, 62, 743-754). In this embodiment, 5 mL of blood was collected from a vein, placed at room temperature for 2 hours, and centrifuged at 3500 g for 15 minutes to obtain serum. Total miRNA was extracted and obtained from 200 μL of serum by a miRNA isolation kit (Cat. No. DP-501, Beijing Tiangen Biochemical) according to the instructions. 2.0 μL of total miRNA, 2.0 μL of a mixed solution of three microspheres containing P-m141 (SEQ ID NO:6 cross-linked with Luminex microsphere LC10001-03), P-m155 (SEQ ID NO: 7 cross-linked with Luminex microsphere LC10001-04), P-M375 (SEQ ID NO: 8 cross-linked with Luminex microsphere LC10001-04) and P-m34a (SEQ ID NO: 10 cross-linked with Luminex microsphere LC10001-07), 1.0 μL of RH3CF at a concentration of 10 nM were added to 15.0 μL of hybridization solution and mixed uniformly. The mixture was reacted at 42° C. for 20 minutes, 80 μL of hybridization dilution was added thereto, transferred to a 96-well plate, and put into Luminex-200 to detect the fluorescent signal. The detections were repeated 5 times, and the results are shown in FIG. 12. The content of miR-34a from this detection is the highest, about 10 nM, which is much higher than the other two, miR-141 and miR-155 that are often used by researchers. It can be seen that in the detection of multiplex biomarkers, especially miRNA, single-tube detection without PCR amplification for multiple miRNAs is more accurate in both qualitative and quantitative detection of biomarkers. This embodiment also verifies the technical contribution of the present disclosure.

Embodiment 14 Single-Tube Simultaneous Detection of Multiplex miRNAs in Blood, Urine and Saliva Venous blood, saliva and urine were collected from the same healthy person, respectively. miRNAs in serum were isolated according to the procedure in Embodiment 4. 1 mL of PBS buffer was added to the saliva, pipetted evenly, and 0.5 mL of the mixture was taken and added with the same volume of Trizol, followed by shaking and mixing uniformly. After the urine was centrifuged at 3500 g for 5 minutes, 0.5 mL of the urine was taken and added with the same volume of Trizol. The mixture was then centrifuged at 12,000 g for 1 minute, 0.2 mL of chloroform was added to the supernatant, shaken and mixed uniformly, and stood still for 2 minutes. The supernatant was collected after centrifuging the mixture at 12,000 g for 15 minutes, the same volume of isopropanol was added thereto, and placed at room temperature for 20 minutes. The supernatant was discarded after centrifuging the mixture at 12,000 g for 5 minutes. The pellets were washed twice with pre-cooled 75% ethanol, and 50 μL of TE was added to dissolve the RNA.

Figure 13A:
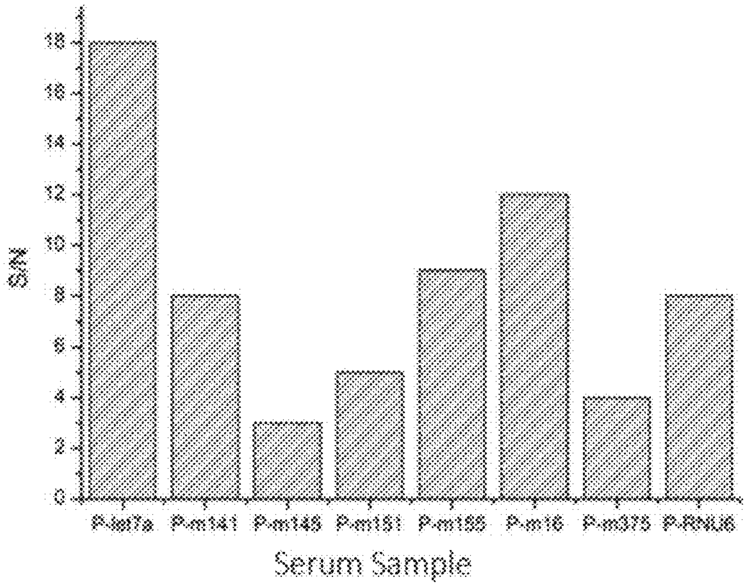
FIGS. 13A-13C respectively show the results of simultaneous detection of multiplex miRNAs in serum, urine and saliva in a single-tube reaction.
Figure 13B:
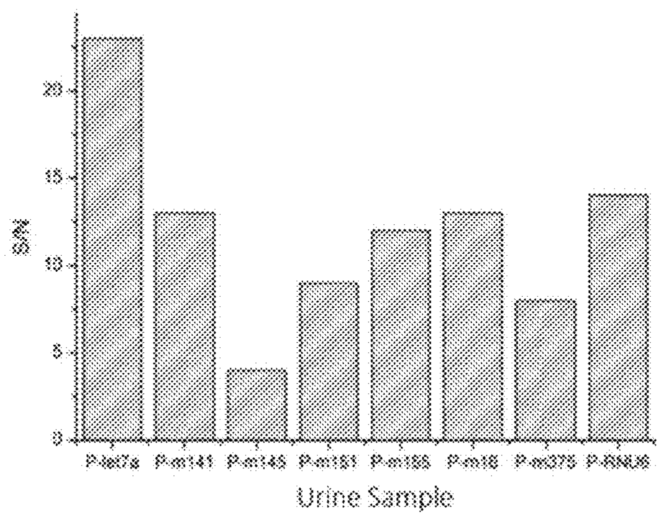
Figure 13C:
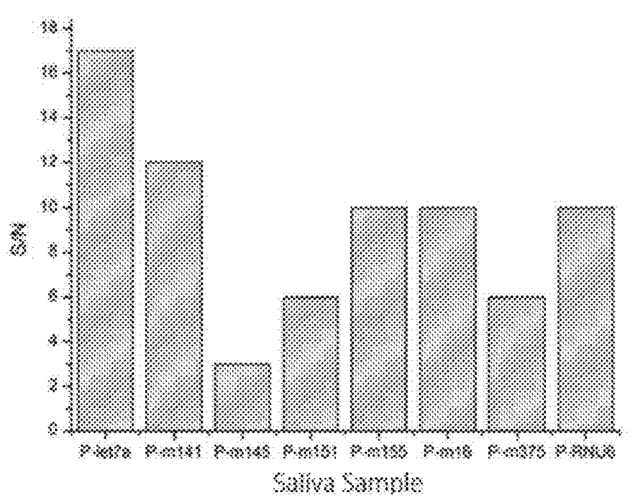

2.0 μL of each RNA extracted from serum, saliva and urine, 2.0 μL of a mixed solution of eight microspheres containing P-let7a (SEQ ID NO: 1 cross-linked with Luminex microsphere LC10001-01), P-m141 (SEQ ID NO: 6 cross-linked with Luminex microsphere LC10001-03), P-m155 (SEQ ID NO:7 cross-linked with Luminex microsphere LC10001-03), P-m375 (SEQ ID NO: 8 cross-linked with Luminex microsphere LC10001-05), P-RNU6 (SEQ ID NO:9 cross-linked with Luminex microsphere LC10001-06), P-m16 (SEQ ID NO: 11 cross-linked with Luminex microsphere LC10001-08), P-m151 (SEQ ID NO: 12 cross-linked with Luminex microsphere LC10001-09) and P-m145 (SEQ ID NO: 13 cross-linked with Luminex microsphere LC10001-10), 1.0 μL of RH3CF at a concentration of 10 nM were added to 15.0 μL of hybridization solution, mixed uniformly, and reacted at 42° C. for 20 minutes, 80 μL of hybridization dilution was added thereto, transferred to a 96-well plate, and put into Luminex-200 to detect the fluorescent signal. The detection was repeated 5 times, and the results are shown in FIGS. 13A-13C. It can be seen that the contents of miR-145 and miR-375 are relatively low, and the contents of miR-16 and let7a are relatively high. Moreover, serum (FIG. 13A), saliva (FIG. 13B) and urine (FIG. 13C) all have abundant miRNAs that can be used as disease-related biomarkers for research.

The 8 kinds of miRNA probes selected in the embodiments of the present disclosure were analyzed for common miRNAs in the research of miRNA biomarkers, which proves the feasibility of simultaneously detecting multiple miRNAs in a single tube. Compared with the traditional Reverse Transcription PCR, in which each reaction tube detects one miRNA at a time, the PCR amplification-free of the present disclosure can detect 8 kinds of miRNAs in one tube. Theoretically, with the increase of the number of probe types, on the Luminex instrument system, a single tube reaction can detect up to 500 kinds of miRNAs, and the Luminex xMAP is equipped with 500 types of microspheres and has the function of detecting 500 different indicators at one time. The application of the present disclosure is also suitable for other multi-index detection instrument systems.

This embodiment analyzed miRNAs from different body fluid sources. Blood, urine and saliva miRNAs may be directly detected. It is verified that liquid biopsy for multiple liquid specimen sources can be achieved through the technology of the present disclosure. Analysis of miRNA biomarkers from urine, which is more convenient and accurate in urinary system diseases, has been widely studied. The detection of miRNA biomarkers in saliva can be applied to the diagnosis and monitoring of diseases such as head and neck cancer.

Therefore, from Embodiments 13 and 14, this technology not only demonstrates the detection of multiple miRNA biomarkers in a single tube, which has advantages over traditional RT-PCR in detection throughput and accuracy, but also can conveniently detect and analyze miRNA in blood, saliva and urine and provide a highly feasible solution for liquid biopsy of miRNA biomarkers.

Figure 14:
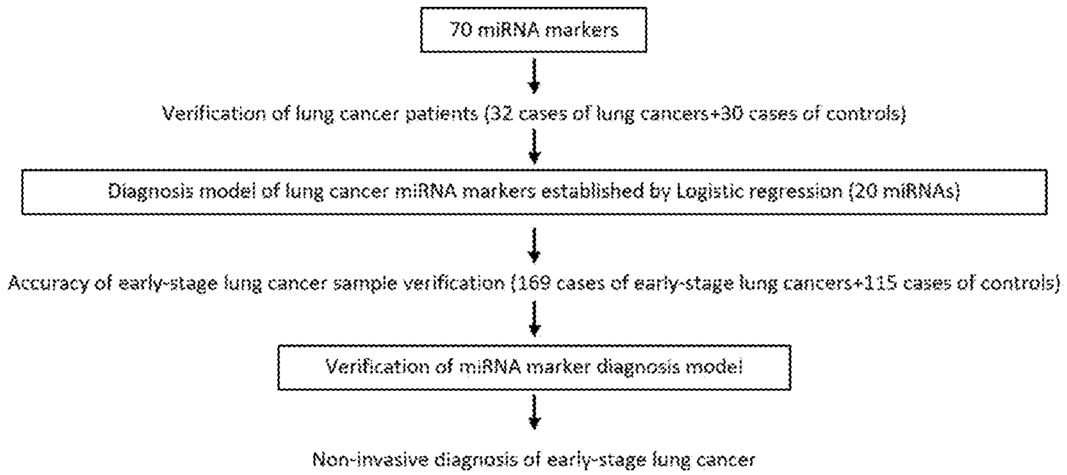
FIG. 14 shows the screening and verification process of lung cancer miRNA biomarkers.

Embodiment 15 Discovery of miRNA Biomarker Combinations and Diagnosis of Lung Cancer I. Collection of Samples and Arrangement of Sample Data The inventors of the present application, according to standard operating procedures (SOP), collected serum samples that met the standards, and systematically collected complete demographic data, clinical data, etc., and by sorting out the sample data, the inventors selected serum samples from 62 people for screening and validation assays of lung cancer miRNA biomarkers. The detection technology utilizes fluorescent cross-linked RNase Hv-(Gly-Gly-Cys-$AF_{532}$)$_3$ (hereinafter referred to as RH3CF) to directly recognize RNA-DNA hybrid strands and convert them to generate detectable signals without PCR amplification (FIG. 14).

II. Screening and miRNA Biomarker Discovery Stage

Among the serum samples of 62 people in the screening and miRNA biomarker discovery stage, 32 people were in the lung cancer group and 30 people were in the control group. The inclusion criteria for the lung cancer group were: newly diagnosed and untreated lung cancer patients diagnosed definitely by pathology, and had not undergone surgery and chemoradiotherapy before blood collection and no preoperative chemoradiotherapy. The inclusion criteria for the 30 people in normal control group were: normal control population with no history of tumor disease, no obvious abnormality after CT screening. The lung cancer group and the normal control group were matched for gender and age. Among the 32 lung cancer samples in the discovery stage, the lung cancers were classified into 21 cases of lung adenocarcinomas, 6 cases of lung squamous cell carcinomas, 2 cases of small cell lung cancers, 2 cases of sarcomatoid carcinomas, and 1 case of lymphoepithelioma-like carcinoma. According to TNM staging, there were 5 in T1 stage, 12 in T2 stage, 3 in T3 stage, and 12 in T4 stage, covering lung cancer cases from early to advanced stages. There were 20 males and 12 females. The average age was 60.8±11.0 years old, the oldest was 73 years old and the youngest was 36 years old.

The detection technology adopted the technology of detecting multiplex miRNAs in a single reaction tube by liquid phase chip, and selected 70 kinds of miRNAs for detection in combination with literature research. The specific process is shown in FIG. 14. All miRNA sequences disclosed in the present disclosure have been stored in the miRBase database (http://www.mirbase.org/).

1. Chip preparation:

Seventy kinds of carboxylated polystyrene microspheres (Cat. No. LC10001-01 to Cat. No. LC10001-70, Luminex Company) were selected, and the probes and the microspheres were covalently cross-linked and coated according to the following method:

(1) The probes were dissolved in double distilled water to a concentration of 100 μM, respectively.

(2) Microsphere washing: 50 μL of each kind of microspheres (containing $6.0\times10^5$ microspheres/mL) were taken, centrifuged under the condition of 10000 g centrifugal force for 5 minutes, and the supernatant was discard. Then 50 μL of 0.1 M MES solution, pH 4.5 was added thereto and shaken for 15 sec to suspend the microspheres, and centrifuged under the condition of 10,000 g centrifugal force for 5 minutes to precipitate the microspheres, the supernatant was discarded. The microspheres were resuspended with 50 μL of 0.1 M MES buffer, pH 4.5.

(3) Covalently cross-linking probes and microspheres: 2.0 μL of 100 μM probes was added to the corresponding microsphere suspension in the previous step, mixed uniformly, 2.5 μL of 10 mg/mL EDC solution was added thereto and reacted at 37° C. for 30 minutes in the dark.

(4) 2.5 μL of 10 mg/mL EDC solution was added thereto again and reacted at 37° C. for 30 minutes in the dark.

(5) Microspheres were precipitated by centrifugation under the condition of 10000 g centrifugal force for 5 minutes. 1.0 mL of 0.1% SDS was added to resuspend the microspheres, mixed uniformly with a shaker, and centrifuged under the condition of 10,000 g centrifugal force for 5 minutes to precipitate the microspheres.

(6) The supernatant was discarded and 100 μL of TE (pH 8.0) was used to resuspend the microspheres.

(7) The coded microspheres coated with different probes were mixed to obtain a liquid phase chip.

2. Extract of serum total RNA: miRNeasy Mini kit (Qiagen, 217184) was used to extract serum total RNA;

3. Mixing: 2.0 μL volume of total RNA obtained in step 2, 2.0 μL of microsphere mixture and 1.0 μL of 10 nM RH3CF were added to 15.0 μL hybridization solution (500 mM NaCl, 0.05% TWEEN® 20, 1 mM $MgCl_2$, 50 mM Tris-HCl, pH 7.5), and mixed uniformly with a vortex for 5 seconds. The standard of each concentration of miRNA let7a was detected in 5 replicates.

4. Liquid-phase chip hybridization reaction: placed in a pre-set 42° C. water bath for 20 minutes.

5. Detection: 80 μL of hybridization diluent (100 mM NaCl, 0.05% TWEEN® 20, 20 mM Tris-HCl, pH 7.5) was added, pipetted into a 96-well plate, and put into Luminex-200 for detection.

6. Data processing. According to the results of the chips, the reading value of each miRNA was compared with the standard curve, and the concentration of each miRNA in each reaction well was obtained, which is the relative expression level of each miRNA in the serum. The miRNA standard curve was obtained by the following experiments: the synthesized miRNA was dissolved in TE solution to a final concentration of 10 μM, and then diluted with TE solution to different concentrations of 50 nM, 20 nM, 10 nM, 500 pM, 200 pM, 100 pM, 50 pM and 20 pM, and then performed hybridization reaction with the miRNA corresponding probe-crosslinked microspheres. Using the method for detecting serum-extracted miRNA in this embodiment, serial dilution solutions of synthetic miRNA of different concentrations were used to replace serum miRNA, the fluorescence value was read, and a standard curve was drawn.

7. Machine Learning and Data Analysis

Figure 15:
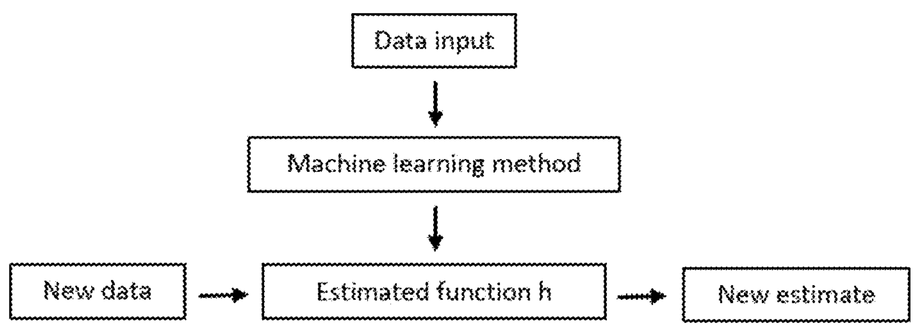
FIG. 15 shows a flowchart of machine learning and model building.

The present disclosure used a typical machine learning process for data analysis, modeling and testing, and adopted the following typical process. In a typical machine learning process, input data was first given, the algorithm may obtain an estimated function by a series of processes, and this function has the ability to give a new estimate for new data that has not been seen, also known as building a model (see FIG. 15).

In general, regression is not used in classification problems, because regression is a continuous model and is more affected by noise. But logistic regression can be used for classification and multi-parameter problem solving. Logistic regression is essentially linear regression, but a layer of function mapping is added to the mapping of features to results, that is, the features are summed linearly, and then the function g(z) is used to predict. g(z) may map continuous values to 0 and 1.

The hypothetical function of logistic regression is as follows, and the hypothetical function of linear regression is just $\theta^T$x.

$$h_\theta(x) = g(\theta^T x) = \frac{1}{1+e^{-\theta^T x}},$$

$$g(z) = \frac{1}{1+e^{-z}}$$

Logistic regression is used to classify 0/1 problems, that is, binary classification problems where the predicted result belongs to 0 or 1. Here it is assumed that the binary values satisfy the Bernoulli distribution, that is:

$$P(y=1|x;\theta)=h_\theta(x)$$

$$P(y=0|x;\theta)=1-h_\theta(x)$$

Therefore, the logistic regression classification algorithm is to establish a regression formula on the data set and to classify based on this. The basic form of a regression classifier is to multiply each feature by a regression coefficient and then add all the resulting values. In this way, the result of the calculation will be a value between 0 and 1. Furthermore, 0.5 or more can be classified into one category, and less can be classified into one category. In the present disclosure, the value of each miRNA represents each feature. The corresponding coefficients for each miRNA were determined by calculating and modeling miRNA data by two types of clinical samples (lung cancer group and non-lung cancer group) with known properties. The 20 recognized miRNA biomarkers used to train the logistic regression yielded the following equations with constant coefficients (β0, β1, β2, β3, β4, . . . βn) and resulted in an $LC_{score}$ from 0 to 1 (continuous). For screening and obtaining the miRNA biomarkers that can effectively distinguish lung cancer and normal controls in the present disclosure, the used logistic regression estimation function $LC_{score}$ is as follows:

$$LC_{score} = \frac{e^y}{1+e^y}$$

wherein, y=β0+β1*C1+ . . . βi*Ci . . . +βn*Cn

Using the principle of logistic regression, from the starting 70 miRNAs, the expression levels (concentrations) of the corresponding miRNAs in each sample collected from the detected 62 samples were used to screen out the feature expression levels of the 20 miRNAs. The numbers and weighted assignments of the 20 miRNAs are shown in Table 4 below:

TABLE 4

Numbers and weighted assignments of miRNAs

| Number (n) | miRNA | Weighted assignment (β) |
|---|---|---|
| 1 | miR-191 | +0.3350 |
| 2 | miR-454 | −0.4206 |
| 3 | miR-1285 | −0.2034 |
| 4 | miR-126 | +0.3019 |
| 5 | miR-181a-2* | +0.1077 |
| 6 | miR-203a | −0.1861 |
| 7 | miR-15b | −0.460 |
| 8 | miR-21 | +0.2339 |
| 9 | miR-365 | −0.0582 |
| 10 | miR-486-5p | +0.2970 |
| 11 | miR-375 | −0.2875 |
| 12 | miR-429 | −0.1120 |
| 13 | miR-141 | +0.0666 |
| 14 | miR-193b | +0.1581 |
| 15 | miR-125b | −0.1142 |
| 16 | miR-206 | −0.0656 |
| 17 | miR-155 | +0.0821 |
| 18 | miR-574-5p | +0.0706 |
| 19 | miR-19a | +0.2011 |
| 20 | miR-200b | +0.0459 |

For example, when n is 2, the analysis module counts the sum of the weighted assignments and the concentration products of miRNAs numbered 1 and 2, namely miR-191 and miR-454, to obtain $LC_{score}=0.5409+\beta_1\times C_1+\beta_2\times C_2=0.5409+0.3350\times C_{miR\text{-}191}-0.4206\times C_{miR\text{-}454}$. Herein, the left side of the operator × is the weighted assignment of each miRNA, and the right side is the concentration (nM) of the miRNA.

When n is 4, the analysis module counts the sum of the weighted assignments and the concentration products of the four miRNAs numbered 1 to 4, to obtain $LC_{score}0.5409+\beta_1\times C_1+\beta_2\times C_2+\beta_3\times C_3+\beta_4\times C_4=0.5409+0.3350\times C_{miR\text{-}191}-0.4206\times C_{miR\text{-}454}-0.2034\times C_{miR\text{-}1285}+0.3019\times C_{miR\text{-}126}$. And so forth.

When 20 miRNAs were analyzed, using the following formula, 30 controls and 32 lung cancers could be distinguished (screening stage in Table 5). $LC_{score}=0.5409-0.1142\times C_{miR\text{-}125b}+0.3019\times C_{miR\text{-}126}-0.2034\times C_{miR\text{-}1285}+0.0666\times C_{miR\text{-}141}+0.0821\times C_{miR\text{-}155}-0.460\times C_{miR\text{-}15b}+0.1077\times C_{miR\text{-}181a\text{-}2*}+0.3350\times C_{miR\text{-}191}+0.1581\times C_{miR\text{-}193b}+0.2011\times C_{miR\text{-}19a}+0.0459\times C_{miR\text{-}200b}-0.1861\times C_{miR\text{-}203a}-0.0656\times C_{miR\text{-}206}+0.2339\times C_{miR\text{-}21}-0.0582\times C_{miR\text{-}365}-0.2875\times C_{miR\text{-}375}-0.1120\times C_{miR\text{-}429}-0.4206\times C_{miR\text{-}454}+0.2970\times C_{miR\text{-}486\text{-}5p}+0.0706\times C_{miR\text{-}574\text{-}5p}$.

Herein, the left side of the operator × is the weighted assignment of each miRNA, and the right side is the concentration (nM) of the miRNA. This formula is also suitable for $LC_{scores}$ detecting miRNA combinations with less than 20 miRNAs. For example, when the number of miRNAs is only 4, the analysis module counts the sum of the weighted assignments and the concentration products of the 4 miRNAs numbered 1 to 4, that is, $LC_{score}=0.5409+\beta_1\times C_1+\beta_2\times C_2+\beta_{33}\times C_3+\beta_4\times C_4=0.5409+0.3350\times C_{miR\text{-}191}-0.4206\times C_{miR\text{-}454}-0.2034\times C_{miR\text{-}1285}+0.3019\times C_{miR\text{-}126}$.

Figure 16:
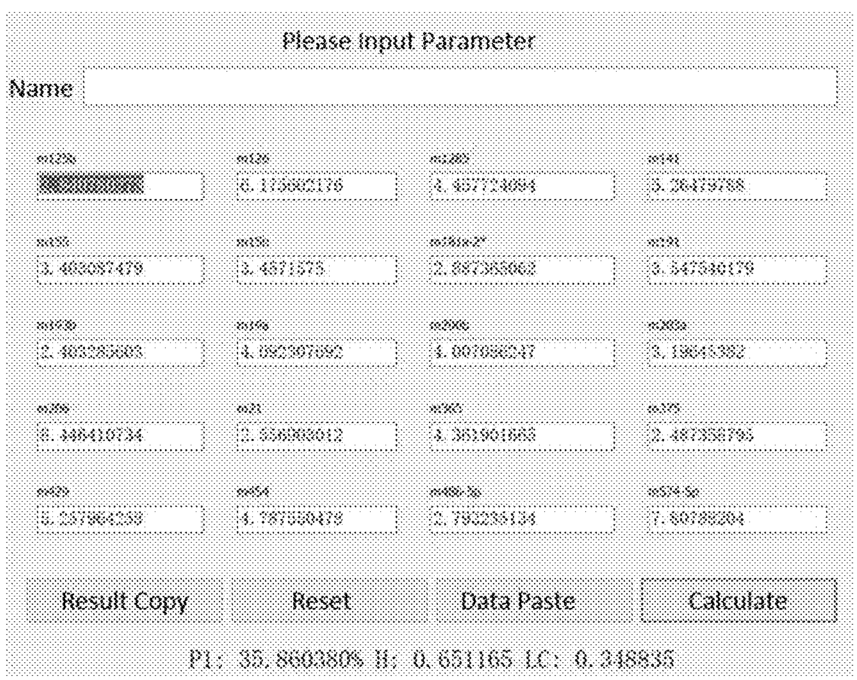
FIG. 16 shows an application interface of the detection device of the lung cancer diagnosis system.

As shown in Table 5, 30 out of 32 lung cancer samples could be correctly classified by the formula. In the table, true positive represents that the miRNA detection result is consistent with the clinical pathological determination of lung cancer, true negative means that the detection result is consistent with the clinical observed negative, false positive means that the miRNA detection result is positive but the clinical observation is negative, and false negative means the detection result is negative but in fact the clinical pathological result is judged to be lung cancer. FIG. 16 shows the application interface of the lung cancer detection device constructed according to the above model.

TABLE 5

Detection performance of 20 miRNA combination biomarkers in discovery and verification stages

| Stage | True positive | True negative | False positive | False negative | Specificity | Sensitivity | Total consistent rate |
|---|---|---|---|---|---|---|---|
| Screening | 30 | 30 | 0 | 2 | 100.0% | 93.8% | 96.8% |
| Verification | 149 | 69 | 46 | 20 | 60.0% | 88.2% | 76.8% |

According to the correlation analysis, miR-126 and miR-454 combination had the highest correlation.

Because the starting 70 miRNAs were obtained from literature research, individual miRNAs were reported by multiple researchers to be associated with the diagnosis of benign and malignant/early-stage lung cancer in pulmonary nodules. However, these well-researched and reported detection technology platforms for miRNAs related to lung cancer diagnosis are based on conventional miRNA ligation and PCR amplification, which have great detection systematic bias (Raabe et al., Nucleic Acids Res. 2014, 42 (3): 1414-1426), so only some of the miRNA changes are true changes. The present disclosure, involving from the previous literature and data analysis, without the need for large-scale screening of clinical samples from the possible thousands of miRNAs, and directly using the multiplex miRNA detection technology without PCR amplification to find out lung cancer diagnosis relevant biomarkers suitable for this detection system and find out the biomarkers of statistical significance, is a methodological innovation and progress in seeking biomarkers for disease diagnosis.

III. Verification Stage

A double-blind control experiment was conducted in the verification stage. The microsphere chips prepared from the 20 miRNAs found in the discovery stage (the corresponding probe sequences are shown in Table 6). Methods of serum isolation, detection and data analysis were used to perform double-blind detection for clinical samples to verify the accuracy of 20 miRNAs screened as lung cancer. The process of double-blind detection was to first give the detection results of whether the patient has lung cancer according to the detection of collected serum, and then compare with the results of clinical cases. A total of 169 patients in the lung cancer group and 115 patients in the control group were selected.

TABLE 6

Probe sequences and modifications thereof for lung cancer diagnosis

| SEQ ID NO: | Name | Sequence (5' → 3') | Modification |
|---|---|---|---|
| 21 | P-m574-5p | acacactcacacacacactcatttttt | 3' NH2-C6 |
| 22 | P-m15b | tgtaaaccatgatgtgctgctatttttt | 3' NH2-C6 |
| 23 | P-m125b | tcacaagttagggtctcagggatttttt | 3' NH2-C6 |
| 24 | P-m193b | agcgggactttgagggccagttttttttt | 3' NH2-C6 |
| 25 | P-m206 | ccacacacttccttacattccatttttt | 3' NH2-C6 |
| 26 | P-m486 | ctcggggcagctcagtacaggatttttt | 3'NH2-C6 |
| 27 | P-m429 | acggttttaccagacagtattatttttt | 3'NH2-C6 |
| 28 | P-m365 | ataaggatttttaggggcattatttttt | 3'NH2-C6 |
| 29 | P-m203a | aactgttgaactgttaagaaccactttttttt | 3'NH2-C6 |
| 30 | P-m454 | accctataagcaatattgcactatttttt | 3'NH2-C6 |
| 31 | P-m1285 | aggtctcactttgttgcccagatttttt | 3'NH2-C6 |
| 32 | P-m126 | cgcattattactcacggtacgatttttt | 3'NH2-C6 |
| 33 | P-m21 | tcaacatcagtctgataagctatttttt | 3'NH2-C6 |
| 34 | P-m19a | tcagttttgcatagatttgcacatttttt | 3'NH2-C6 |
| 35 | P-m200b | tcatcattaccaggcagtattatttttt | 3'NH2-C6 |
| 36 | P-m181a-2* | ggtacagtcaacggtcagtggttttttt | 3'NH2-C6 |
| 37 | P3-m191 | cagctgcttttgggattccgttgtttttt | 3'NH2-C6 |
| 6 | P-m141 | ccatctttaccagacagtgttatttttt | 3'NH2-C6 |
| 7 | P-m155 | acccctatcacgattagcattaatttttt | 3'NH2-C6 |
| 8 | P-m375 | tcacgcgagccgaacgaacaaatttttt | 3'NH2-C6 |

The specific steps to verify the accuracy of 20 miRNAs for lung cancer samples were as follows:

1. Serum total RNA extraction: serum total RNA was extracted from 169 lung cancer patients and 115 in control group, respectively.
2. Mixing: 2.0 μL volume of total RNA obtained in step 1, 2.0 μL of microsphere mixture and 1.0 μL of 10 nM RH3CF were added to 15.0 μL of hybridization solution (500 mM NaCl, 0.05% TWEEN® 20, 1 mM $MgCl_2$, 50 mM Tris-HCl, pH 7.5), and mixed uniformly with a vortex for 5 seconds.
4. Liquid-phase chip hybridization reaction: placed in a pre-set 42° C. water bath for 20 minutes.
5. Detection: 80 μL of hybridization diluent (100 mM NaCl, 0.05% TWEEN® 20, 20 mM Tris-HCl, pH 7.5) was added, pipetted into a 96-well plate, and put into Luminex-200 for detection.
6. Data processing and analysis: According to the results of the chip, the reading value of each miRNA, and the adopted PCA reading value were used as the background to calculate the concentration of the selected 20 miRNAs (unit is nM), representing the relative expression level of the 20 miRNAs in serum. The above-mentioned lung cancer diagnosis formula was used for calculation, the calculation result $LC_{score}\geq 0.5$ was lung cancer, and <0.5 was healthy. The detection results are shown in the verification stage statistics of Table 5. The methods for verifying 1, 2, 4, 6, 8, 10, 12, 14, 16, and 18 miRNAs are the same as above.

62 samples in the discovery stage and 284 samples in the verification stage (346 samples in total in the two stages), 20 miRNA (hereinafter referred to as 20-miR) biomarker combinations were used to judge whether lung cancer was positive, and the specificity, sensitivity and total consistent rate of the corresponding CEA, NSE, CYF21-1, SCC, CA125 and CA199 for a total of 346 samples are shown in Table 7 below. Herein, the positive lung cancer samples were confirmed by postoperative pathology, and 22 samples out of the 145 normal controls were benign by postoperative pathological verification.

TABLE 7

| Performance comparison of corresponding miRNA biomarkers and conventional biomarkers of the samples in the discovery and verification stages | | | | | | | | |
|---|---|---|---|---|---|---|---|---|
| Maker type | Critical value | True positive | True negative | False positive | False negative | Specificity | Sensitivity | Total consistent rate |
| 20 miRNAs | 0.50 | 169 | 110 | 35 | 32 | 75.9% | 84.1% | 80.6% |
| CEA | 5.0 ng/mL | 31 | 138 | 7 | 170 | 95.2% | 15.4% | 48.% |
| NSE | 17.0 ng/mL | 53 | 136 | 9 | 148 | 93.8% | 26.4% | 54.6% |
| CYF21-1 | 3.3 ng/mL | 3 | 145 | 0 | 198 | 100.0% | 1.5% | 42.8% |
| SCC | 1.5 ng/mL | 20 | 133 | 12 | 181 | 91.7% | 10.0% | 44.2% |
| CA125 | 35.0 U/mL | 1 | 145 | 0 | 200 | 100.0% | 0.5% | 42.2% |
| CA199 | 37.0 U/mL | 6 | 145 | 0 | 195 | 100.0% | 3.0% | 43.6% |

In Table 7, true positive represents that the detection results are consistent with the clinical results of lung cancer, true negative means that the detection results are consistent with the clinical observations and are negative, false positive means that the detection results are positive but clinical observations are negative, and false negative means that the detection results are negative but the clinical pathological results are judged as lung cancer. The 284 samples in the verification stage included 169 lung cancer patients and 115 controls, with an average age of 54.3.8±11.8 years old, the oldest being 72 years old and the youngest being 42 years old, including 138 males and 146 females. The lung cancer group was classified into 148 cases of lung adenocarcinoma, 13 cases of lung squamous cell carcinoma, 2 cases of small cell lung cancer, 3 cases of squamous cell carcinoma in situ, 2 cases of small cell carcinoma, and 3 cases of esophageal cancer.

Table 8 shows the detection accuracy of each stage of lung cancer according to TNM staging. Samples were mainly from early-stage lung cancer. Among the 284 samples in the verification stage, the number of cases whose postoperative pathological results were benign was 22. It can be seen that compared with conventional blood biomarkers such as CEA, the biomarker of 20-miR combination has a significant improvement in the detection sensitivity of early-stage lung cancer, up to 84.1%. The overall coincidence rate TTN of the 346 samples also reached 80.6%, which has great application feasibility for the timely detection of early-stage asymptomatic lung cancer.

TABLE 8

| Detection accuracy of miRNA in lung cancer samples of TNM staging at validation stage | | | |
|---|---|---|---|
| Stage | Detected positive (case) | Detected negative (case) | Accuracy/ sensitivity |
| T1 | 134 | 17 | 88.7% |
| T2 | 8 | 2 | 80.0% |
| T3 | 2 | 0 | 100.0% |
| T4 | 6 | 1 | 85.7% |

IV. The Effects of Different Numbers of miRNA Biomarker Combinations on the Judgment of Results The judgment formula $LC_{score}$ based on the 20-miR biomarker for whether lung cancer was positive was obtained by Logistic regression, according to the weight (coefficient) of each miRNA in the formula, the results were re-analyzed with different numbers of miRNAs, and compared with the actual clinical results.

As shown in Table 9, the single miRNA biomarkers were miR-191 and miR-454, and two miRNAs were added each time. For example, the number of 4 miRNA biomarkers (hereinafter referred to as 4-miR) is to add miR-1285 and miR-126 on the basis of miR-191 and miR-454, and the number of 6 miRNA biomarkers is to add miR-181a-2*+ miR-203a on the basis of 4 and finally 20 numbers of miRNAs. All 284 samples were re-analyzed with different combinations of miRNA biomarkers, and the obtained detection results are shown in Table 9 below.

TABLE 9

| The effects of different numbers of miRNA biomarker combinations on the judgment of the results in the verification stage | | | | | | | | | |
|---|---|---|---|---|---|---|---|---|---|
| Number of miRNA | miRNA combination (Number) | Critical value | True positive | True negative | False positive | False negative | Specificity | Sensitivity | Total consistent rate |
| 1 | miR-191 (1) | 0.5 | 101 | 65 | 50 | 68 | 56.5% | 59.8% | 58.5% |
| 1 | miR-454 (2) | 0.5 | 98 | 65 | 50 | 71 | 56.5% | 58.0% | 57.4% |
| 2 | miR-191 + miR-454 | 0.5 | 93 | 62 | 53 | 76 | 53.9% | 55.0% | 54.6% |
| 4 | Adding miR-1285 (3) + miR-126 (4) | 0.5 | 154 | 31 | 84 | 15 | 27.0% | 91.1% | 65.1% |
| 6 | Adding miR-181a-2* (5) + miR-203a (6) | 0.5 | 154 | 38 | 77 | 15 | 33.0% | 91.1% | 67.6% |
| 8 | Adding miR-15b (7) + miR-21 (8) | 0.5 | 152 | 40 | 75 | 17 | 34.8% | 89.9% | 67.6% |

TABLE 9-continued

The effects of different numbers of miRNA biomarker combinations on the judgment of the results in the verification stage

| Number of miRNA | miRNA combination (Number) | Critical value | True positive | True negative | False positive | False negative | Specificity | Sensitivity | Total consistent rate |
|---|---|---|---|---|---|---|---|---|---|
| 10 | Adding miR-365 (9) + miR-486-5p (10) | 0.5 | 146 | 49 | 66 | 23 | 42.6% | 86.4% | 68.7% |
| 12 | Adding miR-375 (11) + miR-429 (12) | 0.5 | 142 | 60 | 55 | 27 | 52.2% | 84.0% | 71.1% |
| 14 | Adding miR-141 (13) + miR-193b (14) | 0.5 | 138 | 64 | 51 | 31 | 55.7% | 81.7% | 71.1% |
| 16 | Adding miR-125b (15) + miR-206 (16) | 0.5 | 137 | 81 | 34 | 32 | 70.4% | 81.1% | 76.8% |
| 18 | Adding miR-155 (17) + miR-574-5p (18) | 0.5 | 140 | 78 | 37 | 29 | 67.8% | 82.8% | 76.8% |
| 20 | Adding miR-19a (19) + miR200b (20) | 0.5 | 139 | 80 | 35 | 30 | 69.6% | 82.2% | 77.1% |

As can be seen from Table 9, the 20 miR combinations were the best in terms of specificity and total consistent rate, reaching 69.6% and 77.1%, respectively, while the 4-miR combination (miR-191/454/1285/126) was the best in terms of sensitivity, up to 91.1%. Even the total consistent rate of a single miRNA (miR-454) for diagnosing lung cancer reached 57.400 which was superior to cytokine biomarkers. The sensitivity of diagnosing lung cancer from single to multiple miRNAs was 55.0-91.1.% which was much higher than that of cytokine-like biomarkers.

The standard of sensitivity/specificity value: the data of the early diagnosis kit for lung cancer of the domestic Kaibaoluo Company: the sensitivity is 40%-60%, the specificity is 900%; the actual value of the foreign Early CDT-Lung Cancer detection kit for the sensitivity is 300%-40% 0%%, specificity is 800%-90%. The performance of the double-blind test in the performance verification stage of the present disclosure is better than those of the two prior art products. Therefore, in the diagnosis of early-stage lung cancer with different tumor biomarkers, miRNA biomarkers not only have better sensitivity than cytokine biomarkers, but also more sensitive than biomarkers that can detect methylation of ctDNA derived from blood.

V. Re-Verification and Prediction of Detection Specificity

Early-stage lung cancer has no obvious symptoms of clinical manifestations, which theoretically cannot rule out that the control group contains some early-stage lung cancers and is not a real non-lung cancer population. Although most of these control groups have been screened by CT images and conventional tumor biomarkers such as CEA, the sensitivity of CT and conventional tumor biomarkers in early-stage lung cancer is low, varying from 0.5-26.4% (see Table 7). Therefore, it is difficult to completely exclude that 100% of the 145 non-lung cancer controls included in the group were non-lung cancer, although 22 cases in the control group were other benign lesions confirmed by postoperative pathology, this part only accounted for 22/145=15.2% of all controls.

Therefore, the calculation and analysis of the data established by this certain degree of uncertainty may have an impact on the specificity of the verification stage. In order to prove this guess, according to this embodiment, whether the high specificity in the screening stage and the obvious decline in the specificity in the verification stage is the bias caused by the qualitative difficulty of the normal control, the population with low risk of lung cancer was selected for re-detection and verification. 42 volunteers aged 17-18 were selected, serums were collected, and the detection results of 20-miR were used for analysis and judgment. 40 of 42 volunteers in the younger age group had the detection results as negative, with a specificity of 95.2%. Although the low risk of lung cancer group selected this time differs greatly from the above 346 screening and verification groups in age factor, the evaluation is insufficiently reasonable, but in view of the fact that the non-lung cancer control group in the full sense is difficult in practice, the 42 detection results of the younger age group can be partially used as corroboration.

Embodiment 16

Non-Fluorescently Labeled RNase H Mutants Realize Detection of RNA by Monoclonal and Polyclonal Antibodies with Fluorescently Labeled His-Tag Anti His-tag monoclonal antibody mAb (Product Cat. No.: D199987-0100, Shanghai Sangong) and anti His-tag rabbit polyclonal antibody pAb (Product Cat. No.: D110002-0025, Shanghai Sangong), 1 mg each, were respectively added with 1 mg/mL of Alexa Fluor™ 532 C5 Maleimide (Cat. No. A10255, Thermo Fisher), protected from light at 30° C., and reacted at room temperature for 1 hour. Then mixtures were centrifuged 3 times with a 10 kDa ultrafiltration tube (Product Cat. No. Microcon YM-10, Millipore) in an Eppendorf 5424R centrifuge under the conditions of 5000 g and 30 min, to remove uncross-linked free Alexa Fluor™ 532 C5 Maleimide, and the obtained products were mainly fluorescently labeled mAb-F and pAb-F.

Figure 17:
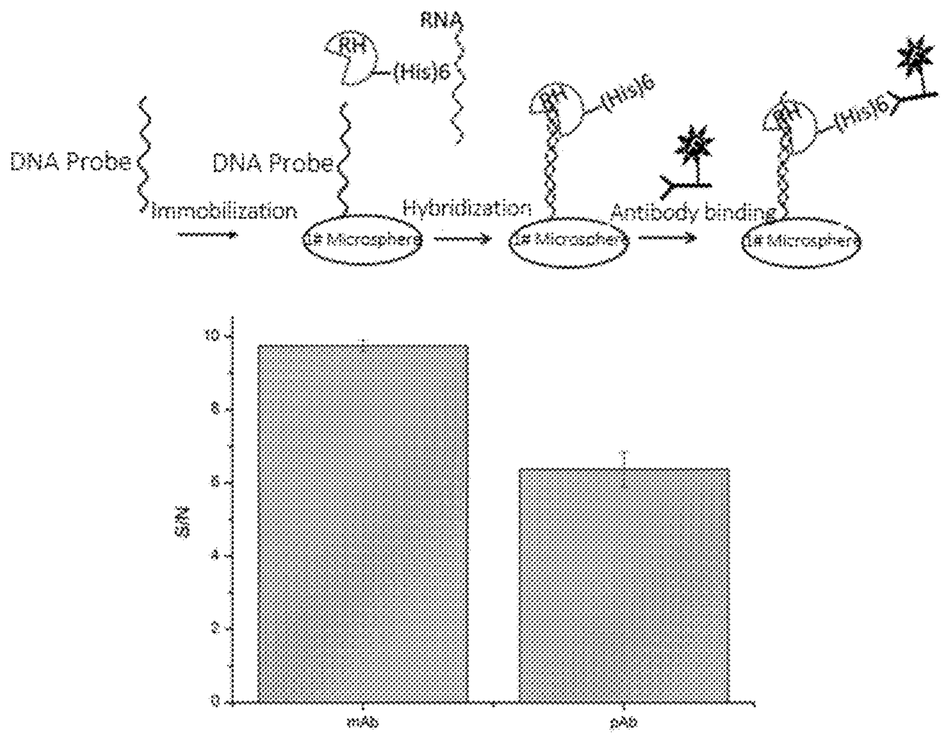
FIG. 17 shows the principle and detection results of RNA detection realized by an RNase H mutant using monoclonal antibodies and polyclonal antibodies capable of recognizing his-tag.

Two sets of identical reactions were set up. 10 nM miRNA let7a, P3-let7a (Table 2, SEQ ID: 1) cross-linked Luminex microspheres LC10001-01 and 1.0 μL of 10 nM RH3C were added to 15.0 μL hybridization solution and mixed uniformly, reacted at 42° C. for 20 minutes. About 50 nM of A532 fluorescently labeled mAb-F and pAb-F were then added thereto, respectively. The reaction was carried out at room temperature for 30 minutes. Then 80 μL of hybridization dilution solution was added thereto, transferred to a 96-microwell plate, and put into Luminex-200 to detect the fluorescent signal. The statistics of 6 detection results are shown in FIG. 17. The fluorescently labeled monoclonal antibody mAb produced a higher signal than polyclonal antibody in detecting the same concentration of RNA. The fluorescently labeled anti-His monoclonal antibody can recognize the His-tagged RH3C, thus detecting the RNA present in the reaction system. Similarly, any tag other than the His tag can be used in the present disclosure as long as the tag can be recognized by any antibody carrying any fluorescent label.

Embodiment 17 Biotin Modified RH3C (Protein ID: 4) and RH5C (Protein ID: 5)

Using the same method in Embodiment 3, Maleimide-PEG11-Biotin (Cat. No. 21911, Thermo Fisher) was cross-linked and purified under the same conditions to obtain a conjugate of RH3C-biotin and RH5C-biotin. RH3C-biotin, RH5C-biotin and RH3CF were tested under the same conditions in Embodiment 7 for the signal generated by let7a miRNA at a final concentration of 1 nM. After the hybridization reaction, 0.2 μL of streptavidin-phycoerythrin complex (Streptavidin, R-Phycoerythrin Conjugate, SAPE) (Cat. No. SA10041, Thermo Fisher) was added thereto to react at room temperature for 10 minutes, so that streptavidin and biotin were combined with each other to carry out a signal test. The detection signals (S/N) obtained from RH3C-biotin, RH5C-biotin and RH3CF were 9.95, 9.15 and 10.13, respectively. The signal generated by RH3C-biotin was stronger than that of RH5C-biotin and was close to that of RH3CF. It can be seen that replacing the fluorescent group with biotin can also realize the application of RNA detection without PCR amplification, and the effect of RH3C-biotin is close to that of RH3CF, but it is necessary to additionally add SAPE to bring in the fluorescent group through the reaction of biotin and streptavidin.

Based on the above embodiments, it can be seen that the RNaseH mutants created by the present disclosure can detect RNA in at least three ways: first, by directly performing site-directed fluorescent labeling on the mutants; secondly, by performing site-directed biotin labeling on the mutants, and then being recognized by molecules that can specifically bind to biotin, such as SAPE; thirdly, by the label carried by the RNaseH mutant, and then being recognized by a fluorescent labeling recognizable tagged antibody.

Embodiment 18 Electronic Device: Tumor Diagnosis Apparatus

This embodiment provides an electronic device 9, that is, a tumor diagnosis apparatus, which can be expressed in the form of a computing device (for example, a server device), and includes a memory, a processor, and a computer program stored in the memory and running on the processor, where the processor, when executing the computer program, can implement the method for cancer diagnosis in Embodiment 15 of the present disclosure.

Figure 18:
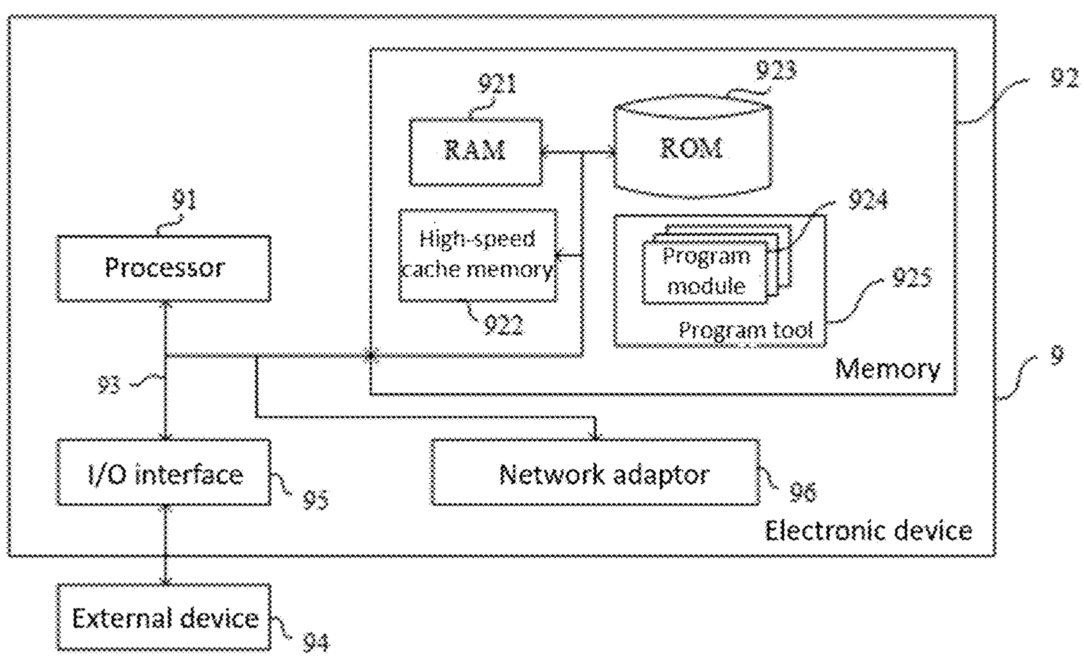
FIG. 18 is a schematic diagram of Embodiment 18.

As shown in FIG. 18, the electronic device 9 specifically includes:

at least one processor 91, at least one memory 92, and a bus 93 for connecting different system components (including the processor 91 and the memory 92), wherein:

the bus 93 includes a data bus, an address bus and a control bus.

The memory 92 includes a volatile memory, such as a random access memory (RAM) 921 and/or a cache memory 922, and may further include a read only memory (ROM) 923.

The memory 92 also includes a program/utility tool 925 having a set (at least one) of program modules 924, such program modules 924 including but not limited to: an operating system, one or more application programs, other program modules, and program data, each or some combination of these examples may include an implementation of a network environment.

The processor 91, by running the computer program stored in the memory 92, executes various functional applications and data processing, for example, the method for cancer diagnosis in Embodiment 15 of the present disclosure.

The electronic device 9 may further communicate with one or more external devices 94 (e.g., a keyboard, a pointing device, etc.). Such communication may take place through an input/output (I/O) interface 95. Also, the electronic device 9 may communicate with one or more networks (e.g., a local area network (LAN), a wide area network (WAN), and/or a public network such as the Internet) through a network adapter 96. The network adapter 96 communicates with other modules of the electronic device 9 via the bus 93. It should be understood that, although not shown in the figures, other hardware and/or software modules may be used in conjunction with the electronic device 9, including but not limited to: a microcode, a device driver, a redundant processor, an external disk drive array, a RAID (disk array) system, a tape drive, and a data backup storage system, etc.

The external device connected to the electronic device 9 also includes a printer, so that the result of the judgment module can be printed by the printer (result printing module) after the diagnosis. In addition, prior to diagnosis, the miRNA results may be input by using a communication means such as a keyboard in the above-mentioned external device 94 or an influencing device (input module), and thus the results can be provided to the analysis module.

It should be noted that although several units/modules or sub-units/modules of the electronic device are mentioned in the above detailed description, this division is merely exemplary and not mandatory. Indeed, according to embodiments of the present application, the features and functions of two or more units/modules described above may be embodied in one unit/module. Conversely, the features and functions of one unit/module described above may be further subdivided to be embodied by multiple units/modules.

Embodiment 19 Computer-Readable Storage Medium

This embodiment provides a computer-readable storage medium on which a computer program is stored, and when the program is executed by a processor, the steps of the method for cancer diagnosis in Embodiment 15 can be implemented.

Herein, the readable storage media may include, but are not limited to: a portable disk, a hard disk, a random access memory, a read-only memory, an erasable programmable read-only memory, an optical storage device, a magnetic storage device, or any of the above suitable combinations.

In a possible implementation, the present disclosure can also be implemented in the form of a program product, which includes a program code, and when the program product runs on a terminal device, the program code is used to cause the terminal device to execute the steps to implement the method for cancer diagnosis of Embodiment 15 of the present disclosure.

Herein, the program code for executing the present disclosure may be written in any combination of one or more programming languages, and the program code can be completely executed on a user device, partially executed on the user device, executed as an independent software package, partially executed on the user device and partially executed on a remote device, or completely executed on the remote device.

What is claimed is:

1. A fluorescent cross-linked RNase H mutant conjugate, wherein the fluorescent cross-linked RNase H mutant conjugate is:

(i) RNase Hv-($L_x$-SH-F)$_n$, or (ii) composed of an RNase Hv-($L_x$-SH-ligand)$_n$ or RNase Hv-($L_x$-SH)$_n$-ligand, and a receptor-F, wherein the ligand can bind to the receptor;

wherein:

RNase Hv is an RNase H mutant, which can bind to RNA or an RNA-DNA hybrid strand, but cannot cleave RNA, and has an amino acid sequence shown in SEQ ID NO: 20;

$L_x$ is Gly, Gly-Gly, Gly-Gly-Gly or Ala-Gly;

SH is an amino acid containing a sulfhydryl group;

F is a luminescent functional group, and n is 3-5.

2. The fluorescent cross-linked RNase H mutant conjugate of claim 1, wherein the fluorescent cross-linked RNase H mutant conjugate satisfies one or more of the following conditions: (i) the SH is cysteine; and (ii) the ligand and the receptor are biotin and streptavidin respectively, or Tag and anti-Tag-Ab respectively.

3. The fluorescent cross-linked RNase H mutant conjugate of claim 2, wherein, in the fluorescent cross-linked RNase H mutant conjugate, ($L_x$-SH-F)$_n$, ($L_x$-SH-ligand)$_n$ or an ($L_x$-SH)$_n$-ligand is linked to C-terminal or N-terminal of the RNase Hv; the anti-Tag-Ab is a rabbit antibody or a human antibody, or the anti-Tag-Ab is a monoclonal antibody or a polyclonal antibody.

4. The fluorescent cross-linked RNase H mutant conjugate of claim 1, wherein, in the fluorescent cross-linked RNase H mutant conjugate, (i) the F is a luminescent substance with an excitation wavelength between 300 nm and 700 nm and an emission wavelength between 300 nm and 700 nm, that can be covalently cross-linked with the SH; or, (ii) the F is phycoerythrin and forms a streptavidin-phycoerythrin complex with streptavidin.

5. A method for preparing the fluorescent cross-linked RNase H mutant conjugate of claim 1, wherein (i) when the fluorescent cross-linked RNase H mutant conjugate is RNase Hv-($L_x$-SH-F)$_n$, then the method comprises following steps:

(1) mixing (Lx-SH)$_n$ and RNase Hv in proportion to conjugate to obtain RNase Hv-($L_x$-SH)$_n$;

(2) adding 2-10 times excessive F to the RNase Hv-($L_x$-SH-)$_n$ obtained in step (1), thereby producing the RNase Hv-($L_x$-SH-F)$_n$;

or, the method comprises following steps:

(1) expressing RNase Hv with (Lx-SH)$_n$ at N-terminal or C-terminal to obtain RNase Hv-($L_x$-SH)$_n$;

(2) adding 2-10 times excessive F, thereby producing the RNase Hv-($L_x$-SH-F)$_n$;

(ii) when the fluorescent cross-linked RNase H mutant conjugate comprises an RNase Hv-($L_x$-SH-ligand)$_n$ or RNase Hv-($L_x$-SH)$_n$-ligand, and a receptor-F, then the method comprises following steps:

(1) expressing RNase Hv with (Lx-SH)$_n$ at N-terminal or C-terminal to obtain RNase Hv-($L_x$-SH)$_n$; connecting the RNase Hv-($L_x$-SH)$_n$ with a ligand to form the RNase Hv-($L_x$-SH-ligand)$_n$ or RNase Hv-($L_x$-SH)$_n$-ligand;

(2) mixing the receptor with 2-10 times excessive F to produce the receptor-F.

6. A kit for RNA detection, wherein the kit comprises the fluorescent cross-linked RNase H mutant conjugate of claim 1.

7. A method for RNA detection comprising the use of the fluorescent cross-linked RNase H mutant conjugate of claim 1, comprising following steps:

when the fluorescent cross-linked RNase H mutant conjugate is RNase Hv-($L_x$-SH-F)$_n$, (1) hybridizing a DNA probe with RNA, and then adding the fluorescent cross-linked RNase H mutant conjugate of claim 1; or, (2) simultaneously adding a DNA probe and RNA, and the fluorescent cross-linked RNase H mutant conjugate of claim 1; and obtaining a detection result by detecting fluorescence;

when the fluorescent cross-linked RNase H mutant conjugate comprises an RNase Hv-($L_x$-SH-ligand)$_n$ or RNase Hv-($L_x$-SH)$_n$-ligand, and a receptor-F, simultaneously adding a DNA probe and RNA, and the RNase Hv-($L_x$-SH-ligand)$_n$ or RNase Hv-($L_x$-SH)$_n$-ligand, after a hybrid strand formed by DNA and RNA is combined with the RNase Hv-($L_x$-SH-ligand)$_n$ or RNase Hv-($L_x$-SH)$_n$-ligand, adding 2-10 times excessive receptor-F, obtaining a detection result by detecting fluorescence.

8. The fluorescent cross-linked RNase H mutant conjugate of claim 1, wherein the fluorescent cross-linked RNase H mutant conjugate is selected from the group consisting of:

(a) RNase Hv-($L_x$-SH-F)$_n$; wherein $L_x$ is Gly, Gly-Gly, Gly-Gly-Gly or Ala-Gly, and n is 3-5, (b) a fluorescent cross-linked RNase H mutant conjugate composed of an RNase Hv-($L_x$-SH-ligand)$_n$ and a receptor-F, wherein the ligand can bind to the receptor, the ligand and the receptor are biotin and streptavidin respectively, $L_x$ is Gly-Gly, and n is 3-5; and (c) a fluorescent cross-linked RNase H mutant conjugate composed of an RNase Hv-($L_x$-SH)$_n$-ligand and a receptor-F, wherein the ligand can bind to the receptor, the ligand and the receptor are Tag and anti-Tag-Ab respectively, $L_x$ is Gly-Gly, and n is 3;

wherein:

RNase Hv is an RNase H mutant, which can bind to RNA or an RNA-DNA hybrid strand, but cannot cleave RNA, and has an amino acid sequence shown in SEQ ID NO: 20;

SH is an amino acid containing a sulfhydryl group; and

F is a luminescent functional group.

9. The fluorescent cross-linked RNase H mutant conjugate of claim 8, wherein the F is a luminescent substance with an excitation wavelength between 480 nm and 580 nm and an emission wavelength between 520 nm and 680 nm.

10. The fluorescent cross-linked RNase H mutant conjugate of claim 8, wherein the F is Alexa Fluor 555 or Alexa Fluor 532; or wherein the Tag is a his Tag.

11. The method of claim 5, wherein the F is Alexa Fluor 555 or Alexa Fluor 532.

12. The kit of claim 6, wherein the kit further comprises a DNA probe, and the 3' end of the DNA probe is immobilized on a microsphere or a flat medium.

13. The method of claim 7, wherein the method satisfies one or more of the following conditions:

(1) the DNA probe and the fluorescent cross-linked RNase H mutant conjugate have a ratio of 2000-100000:1;

(2) the RNA detection is a single-tube detection or multi-tube detection of multiplex RNAs; the single-tube detection is to detect one or more kinds of RNAs in one reaction, and the multi-tube detection is to detect only one kind of RNA in each reaction; and (3) the DNA probe is an immobilized DNA probe, and the immobilized DNA probe is immobilized on a microsphere or a flat medium; or, the RNA is mRNA, non-coding RNA or miRNA.

14. The method of claim 13, wherein the method satisfies one or more of the following conditions:

(1) 3' end of the immobilized DNA probe is immobilized on a microsphere or a flat medium; and (2) the miRNA is a mature miRNA or a precursor miRNA.

* * * * *

SEQUENCE LISTING

<160> NUMBER OF SEQ ID NOS: 37

<210> SEQ ID NO 1
<211> LENGTH: 28
<212> TYPE: DNA
<213> ORGANISM: Artificial Sequence
<220> FEATURE:
<223> OTHER INFORMATION: P3-let7a
<220> FEATURE:
<221> NAME/KEY: misc_feature
<222> LOCATION: (28)..(28)
<223> OTHER INFORMATION: 3' NH2-C6

<400> SEQUENCE: 1
aactatacaa cctactacct catttttt 28

<210> SEQ ID NO 2
<211> LENGTH: 28
<212> TYPE: DNA
<213> ORGANISM: Artificial Sequence
<220> FEATURE:
<223> OTHER INFORMATION: P5-let7a
<220> FEATURE:
<221> NAME/KEY: misc_feature
<222> LOCATION: (28)..(28)
<223> OTHER INFORMATION: 5' NH2-C6

<400> SEQUENCE: 2
ttttttaact atacaaccta ctacctca 28

<210> SEQ ID NO 3
<211> LENGTH: 28
<212> TYPE: DNA
<213> ORGANISM: Artificial Sequence
<220> FEATURE:
<223> OTHER INFORMATION: P3-LNA-let7a
<220> FEATURE:
<221> NAME/KEY: misc_feature
<222> LOCATION: (28)..(28)
<223> OTHER INFORMATION: 3' NH2-C6

<400> SEQUENCE: 3
aactatacaa cctactacct catttttt 28

<210> SEQ ID NO 4
<211> LENGTH: 27
<212> TYPE: DNA
<213> ORGANISM: Artificial Sequence
<220> FEATURE:
<223> OTHER INFORMATION: P3-1a
<220> FEATURE:
<221> NAME/KEY: misc_feature
<222> LOCATION: (27)..(27)
<223> OTHER INFORMATION: 3' NH2-C6

<400> SEQUENCE: 4
ggagtctcca aagccacgta cttttt 27

<210> SEQ ID NO 5
<211> LENGTH: 28
<212> TYPE: DNA
<213> ORGANISM: Artificial Sequence
<220> FEATURE:
<223> OTHER INFORMATION: P-let7b
<220> FEATURE:
<221> NAME/KEY: misc_feature
<222> LOCATION: (28)..(28)
<223> OTHER INFORMATION: 3' NH2-C6

<400> SEQUENCE: 5
aaccacacaa cctactacct catttttt 28

<210> SEQ ID NO 6
<211> LENGTH: 28
<212> TYPE: DNA
<213> ORGANISM: Artificial Sequence
<220> FEATURE:
<223> OTHER INFORMATION: P-m141
<220> FEATURE:
<221> NAME/KEY: misc_feature
<222> LOCATION: (28)..(28)
<223> OTHER INFORMATION: 3' NH2-C6

<400> SEQUENCE: 6
ccatctttac cagacagtgt tatttttt 28

<210> SEQ ID NO 7
<211> LENGTH: 29
<212> TYPE: DNA
<213> ORGANISM: Artificial Sequence
<220> FEATURE:
<223> OTHER INFORMATION: P-m155
<220> FEATURE:
<221> NAME/KEY: misc_feature
<222> LOCATION: (29)..(29)
<223> OTHER INFORMATION: 3' NH2-C6

<400> SEQUENCE: 7
acccctatca cgattagcat taattttt 29

<210> SEQ ID NO 8
<211> LENGTH: 28
<212> TYPE: DNA
<213> ORGANISM: Artificial Sequence
<220> FEATURE:
<223> OTHER INFORMATION: P-m375
<220> FEATURE:
<221> NAME/KEY: misc_feature
<222> LOCATION: (28)..(28)
<223> OTHER INFORMATION: 3' NH2-C6

<400> SEQUENCE: 8
tcacgcgagc cgaacgaaca aatttttt 28

<210> SEQ ID NO 9
<211> LENGTH: 30
<212> TYPE: DNA
<213> ORGANISM: Artificial Sequence
<220> FEATURE:
<223> OTHER INFORMATION: P-RNU6
<220> FEATURE:
<221> NAME/KEY: misc_feature
<222> LOCATION: (30)..(30)
<223> OTHER INFORMATION: 3' NH2-C6

<400> SEQUENCE: 9
ccaattttag tatatgtgct gccgtttttt 30

<210> SEQ ID NO 10
<211> LENGTH: 28
<212> TYPE: DNA

-continued

<213> ORGANISM: Artificial Sequence
<220> FEATURE:
<223> OTHER INFORMATION: P-m34a
<220> FEATURE:
<221> NAME/KEY: misc_feature
<222> LOCATION: (28)..(28)
<223> OTHER INFORMATION: 3' NH2-C6

<400> SEQUENCE: 10
acaaccagct aagacactgc catttttt 28

<210> SEQ ID NO 11
<211> LENGTH: 28
<212> TYPE: DNA
<213> ORGANISM: Artificial Sequence
<220> FEATURE:
<223> OTHER INFORMATION: P-m16
<220> FEATURE:
<221> NAME/KEY: misc_feature
<222> LOCATION: (28)..(28)
<223> OTHER INFORMATION: 3' NH2-C6

<400> SEQUENCE: 11
cgccaatatt tacgtgctgc tatttttt 28

<210> SEQ ID NO 12
<211> LENGTH: 27
<212> TYPE: DNA
<213> ORGANISM: Artificial Sequence
<220> FEATURE:
<223> OTHER INFORMATION: P-m151
<220> FEATURE:
<221> NAME/KEY: misc_feature
<222> LOCATION: (27)..(27)
<223> OTHER INFORMATION: 3' NH2-C6

<400> SEQUENCE: 12
cctcaaggag cttcagtcta gtttttt 27

<210> SEQ ID NO 13
<211> LENGTH: 29
<212> TYPE: DNA
<213> ORGANISM: Artificial Sequence
<220> FEATURE:
<223> OTHER INFORMATION: P-m145
<220> FEATURE:
<221> NAME/KEY: misc_feature
<222> LOCATION: (29)..(29)
<223> OTHER INFORMATION: 3' NH2-C6

<400> SEQUENCE: 13
agggattcct gggaaaactg gactttttt 29

<210> SEQ ID NO 14
<211> LENGTH: 22
<212> TYPE: RNA
<213> ORGANISM: Artificial Sequence
<220> FEATURE:
<223> OTHER INFORMATION: let-7a

<400> SEQUENCE: 14
ugagguagua gguuguauag uu 22

<210> SEQ ID NO 15
<211> LENGTH: 23
<212> TYPE: RNA
<213> ORGANISM: Artificial Sequence
<220> FEATURE:
<223> OTHER INFORMATION: m155

<400> SEQUENCE: 15
uuaaugcuaa ucgugauagg ggu 23

<210> SEQ ID NO 16
<211> LENGTH: 22
<212> TYPE: RNA
<213> ORGANISM: Artificial Sequence
<220> FEATURE:
<223> OTHER INFORMATION: m141

<400> SEQUENCE: 16
uaacacuguc ugguaaagau gg 22

<210> SEQ ID NO 17
<211> LENGTH: 25
<212> TYPE: DNA
<213> ORGANISM: Artificial Sequence
<220> FEATURE:
<223> OTHER INFORMATION: Rp

<400> SEQUENCE: 17
ggaagacaat cttcatctcc ttctg 25

<210> SEQ ID NO 18
<211> LENGTH: 149
<212> TYPE: DNA
<213> ORGANISM: Artificial Sequence
<220> FEATURE:
<223> OTHER INFORMATION: RCA-1a

<400> SEQUENCE: 18
aagattgtgt tgggaaggat ggatggatgt ttaagatgtt gaggtgggtg tgataagagg 60
tggtggaggg agtgtggaaa gggaggtagg ttagtttttt tggatggatg gttgtaatag 120
gagtgagtat agggagagag aaggagatg 149

<210> SEQ ID NO 19
<211> LENGTH: 64
<212> TYPE: RNA
<213> ORGANISM: Artificial Sequence
<220> FEATURE:
<223> OTHER INFORMATION: 1a

<400> SEQUENCE: 19
guacguggcu uuggagacuc cguggaggag gucuuaucag aggcacguca acaucuuaaa 60
gaug 64

<210> SEQ ID NO 20
<211> LENGTH: 155
<212> TYPE: PRT
<213> ORGANISM: Artificial Sequence
<220> FEATURE:
<223> OTHER INFORMATION: E48Q

<400> SEQUENCE: 20

Met Leu Lys Gln Val Glu Ile Phe Thr Asp Gly Ser Cys Leu Gly Asn
1 5 10 15

Pro Gly Pro Gly Gly Tyr Gly Ala Ile Leu Arg Tyr Arg Gly Arg Glu
20 25 30

Lys Thr Phe Ser Ala Gly Tyr Thr Arg Thr Thr Asn Asn Arg Met Gln
35 40 45

Leu Met Ala Ala Ile Val Ala Leu Glu Ala Leu Lys Glu His Cys Glu

-continued

```
    50                  55                  60

Val Ile Leu Ser Thr Asp Ser Gln Tyr Val Arg Gln Gly Ile Thr Gln
65                  70                  75                  80

Trp Ile His Asn Trp Lys Lys Arg Gly Trp Lys Thr Ala Asp Lys Lys
                85                  90                  95

Pro Val Lys Asn Val Asp Leu Trp Gln Arg Leu Asp Ala Ala Leu Gly
            100                 105                 110

Gln His Gln Ile Lys Trp Glu Trp Val Lys Gly His Ala Gly His Pro
        115                 120                 125

Glu Asn Glu Arg Cys Asp Glu Leu Ala Arg Ala Ala Ala Met Asn Pro
    130                 135                 140

Thr Leu Glu Asp Thr Gly Tyr Gln Val Glu Val
145                 150                 155


<210> SEQ ID NO 21
<211> LENGTH: 29
<212> TYPE: DNA
<213> ORGANISM: Artificial Sequence
<220> FEATURE:
<223> OTHER INFORMATION: P-m574-5p
<220> FEATURE:
<221> NAME/KEY: misc_feature
<222> LOCATION: (29)..(29)
<223> OTHER INFORMATION: 3' NH2-C6

<400> SEQUENCE: 21

acacactcac acacacacac tcatttttt                                        29


<210> SEQ ID NO 22
<211> LENGTH: 28
<212> TYPE: DNA
<213> ORGANISM: Artificial Sequence
<220> FEATURE:
<223> OTHER INFORMATION: P-m15b
<220> FEATURE:
<221> NAME/KEY: misc_feature
<222> LOCATION: (28)..(28)
<223> OTHER INFORMATION: 3' NH2-C6

<400> SEQUENCE: 22

tgtaaaccat gatgtgctgc tatttttt                                         28


<210> SEQ ID NO 23
<211> LENGTH: 28
<212> TYPE: DNA
<213> ORGANISM: Artificial Sequence
<220> FEATURE:
<223> OTHER INFORMATION: P-m125b
<220> FEATURE:
<221> NAME/KEY: misc_feature
<222> LOCATION: (28)..(28)
<223> OTHER INFORMATION: 3' NH2-C6

<400> SEQUENCE: 23

tcacaagtta gggtctcagg gatttttt                                         28


<210> SEQ ID NO 24
<211> LENGTH: 28
<212> TYPE: DNA
<213> ORGANISM: Artificial Sequence
<220> FEATURE:
<223> OTHER INFORMATION: P-m193b
<220> FEATURE:
<221> NAME/KEY: misc_feature
<222> LOCATION: (28)..(28)
<223> OTHER INFORMATION: 3' NH2-C6
```

<400> SEQUENCE: 24
agcgggactt tgagggccag tttttttt 28

<210> SEQ ID NO 25
<211> LENGTH: 28
<212> TYPE: DNA
<213> ORGANISM: Artificial Sequence
<220> FEATURE:
<223> OTHER INFORMATION: P-m206
<220> FEATURE:
<221> NAME/KEY: misc_feature
<222> LOCATION: (28)..(28)
<223> OTHER INFORMATION: 3' NH2-C6

<400> SEQUENCE: 25
ccacacactt ccttacattc catttttt 28

<210> SEQ ID NO 26
<211> LENGTH: 28
<212> TYPE: DNA
<213> ORGANISM: Artificial Sequence
<220> FEATURE:
<223> OTHER INFORMATION: P-m486
<220> FEATURE:
<221> NAME/KEY: misc_feature
<222> LOCATION: (28)..(28)
<223> OTHER INFORMATION: 3' NH2-C6

<400> SEQUENCE: 26
ctcggggcag ctcagtacag gatttttt 28

<210> SEQ ID NO 27
<211> LENGTH: 28
<212> TYPE: DNA
<213> ORGANISM: Artificial Sequence
<220> FEATURE:
<223> OTHER INFORMATION: P-m429
<220> FEATURE:
<221> NAME/KEY: misc_feature
<222> LOCATION: (28)..(28)
<223> OTHER INFORMATION: 3' NH2-C6

<400> SEQUENCE: 27
acggttttac cagacagtat tatttttt 28

<210> SEQ ID NO 28
<211> LENGTH: 28
<212> TYPE: DNA
<213> ORGANISM: Artificial Sequence
<220> FEATURE:
<223> OTHER INFORMATION: P-m365
<220> FEATURE:
<221> NAME/KEY: misc_feature
<222> LOCATION: (28)..(28)
<223> OTHER INFORMATION: 3' NH2-C6

<400> SEQUENCE: 28
ataaggattt ttaggggcat tatttttt 28

<210> SEQ ID NO 29
<211> LENGTH: 31
<212> TYPE: DNA
<213> ORGANISM: Artificial Sequence
<220> FEATURE:
<223> OTHER INFORMATION: P-m203a
<220> FEATURE:
<221> NAME/KEY: misc_feature
<222> LOCATION: (31)..(31)

<223> OTHER INFORMATION: 3' NH2-C6

<400> SEQUENCE: 29
aactgttgaa ctgttaagaa ccactttttt t 31

<210> SEQ ID NO 30
<211> LENGTH: 29
<212> TYPE: DNA
<213> ORGANISM: Artificial Sequence
<220> FEATURE:
<223> OTHER INFORMATION: P-m454
<220> FEATURE:
<221> NAME/KEY: misc_feature
<222> LOCATION: (29)..(29)
<223> OTHER INFORMATION: 3' NH2-C6

<400> SEQUENCE: 30
accctataag caatattgca ctattttt 29

<210> SEQ ID NO 31
<211> LENGTH: 28
<212> TYPE: DNA
<213> ORGANISM: Artificial Sequence
<220> FEATURE:
<223> OTHER INFORMATION: P-m1285
<220> FEATURE:
<221> NAME/KEY: misc_feature
<222> LOCATION: (28)..(28)
<223> OTHER INFORMATION: 3' NH2-C6

<400> SEQUENCE: 31
aggtctcact ttgttgccca gatttttt 28

<210> SEQ ID NO 32
<211> LENGTH: 28
<212> TYPE: DNA
<213> ORGANISM: Artificial Sequence
<220> FEATURE:
<223> OTHER INFORMATION: P-m126
<220> FEATURE:
<221> NAME/KEY: misc_feature
<222> LOCATION: (28)..(28)
<223> OTHER INFORMATION: 3' NH2-C6

<400> SEQUENCE: 32
cgcattatta ctcacggtac gatttttt 28

<210> SEQ ID NO 33
<211> LENGTH: 28
<212> TYPE: DNA
<213> ORGANISM: Artificial Sequence
<220> FEATURE:
<223> OTHER INFORMATION: P-m21
<220> FEATURE:
<221> NAME/KEY: misc_feature
<222> LOCATION: (28)..(28)
<223> OTHER INFORMATION: 3' NH2-C6

<400> SEQUENCE: 33
tcaacatcag tctgataagc tatttttt 28

<210> SEQ ID NO 34
<211> LENGTH: 29
<212> TYPE: DNA
<213> ORGANISM: Artificial Sequence
<220> FEATURE:
<223> OTHER INFORMATION: P-m19a
<220> FEATURE:
<221> NAME/KEY: misc_feature -continued

```
<222> LOCATION: (29)..(29)
<223> OTHER INFORMATION: 3' NH2-C6

<400> SEQUENCE: 34

tcagttttgc atagatttgc acatttttt                                        29


<210> SEQ ID NO 35
<211> LENGTH: 28
<212> TYPE: DNA
<213> ORGANISM: Artificial Sequence
<220> FEATURE:
<223> OTHER INFORMATION: P-m200b
<220> FEATURE:
<221> NAME/KEY: misc_feature
<222> LOCATION: (28)..(28)
<223> OTHER INFORMATION: 3' NH2-C6

<400> SEQUENCE: 35

tcatcattac caggcagtat tatttttt                                         28


<210> SEQ ID NO 36
<211> LENGTH: 28
<212> TYPE: DNA
<213> ORGANISM: Artificial Sequence
<220> FEATURE:
<223> OTHER INFORMATION: P-m181a-2*
<220> FEATURE:
<221> NAME/KEY: misc_feature
<222> LOCATION: (28)..(28)
<223> OTHER INFORMATION: 3' NH2-C6

<400> SEQUENCE: 36

ggtacagtca acggtcagtg gttttttt                                         28


<210> SEQ ID NO 37
<211> LENGTH: 29
<212> TYPE: DNA
<213> ORGANISM: Artificial Sequence
<220> FEATURE:
<223> OTHER INFORMATION: P3-m191
<220> FEATURE:
<221> NAME/KEY: misc_feature
<222> LOCATION: (29)..(29)
<223> OTHER INFORMATION: 3' NH2-C6

<400> SEQUENCE: 37

cagctgcttt tgggattccg ttgtttttt                                        29
```